US 8,387,184 B2

(12) United States Patent
Turner et al.

(10) Patent No.: US 8,387,184 B2
(45) Date of Patent: Mar. 5, 2013

(54) AUTO CONTOUR HANDLE APPARATUS

(75) Inventors: Jonathan D. Turner, Dillsboro, IN (US); Richard H. Heimbrock, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 24 days.

(21) Appl. No.: 13/154,697

(22) Filed: Jun. 7, 2011

(65) Prior Publication Data

US 2011/0231997 A1    Sep. 29, 2011

Related U.S. Application Data

(63) Continuation of application No. 11/622,069, filed on Jan. 11, 2007, now Pat. No. 8,069,513.

(60) Provisional application No. 60/760,343, filed on Jan. 19, 2006, provisional application No. 60/804,227, filed on Jun. 8, 2006.

(51) Int. Cl.
    *A47B 7/02* (2006.01)
(52) U.S. Cl. ................................ 5/618; 5/617; 5/613
(58) Field of Classification Search .............. 5/613, 617, 5/618
    See application file for complete search history.

(56) References Cited

U.S. PATENT DOCUMENTS

| RE10,906 E | 3/1888 | Case |
|---|---|---|
| 1,398,203 A | 11/1921 | Schmidt |
| 2,304,199 A | 12/1942 | Pinnow |
| 2,379,080 A | 6/1945 | Hillenbrand |
| 2,500,742 A | 3/1950 | Taylor |
| 2,779,951 A | 2/1957 | Travis |
| 2,913,738 A | 11/1959 | Wise |
| 3,094,713 A | 6/1963 | Wise |
| 3,184,765 A | 5/1965 | Katz |
| 3,253,285 A | 5/1966 | Fox |
| 3,305,877 A | 2/1967 | Nielsen |
| 3,319,270 A | 5/1967 | Greiner |
| 3,353,193 A | 11/1967 | Greiner |
| 3,589,715 A | 6/1971 | Mark et al. |
| 3,665,528 A | 5/1972 | Kjellberg et al. |
| 3,872,945 A | 3/1975 | Hickman et al. |
| 3,916,461 A | 11/1975 | Kerstholt |
| 3,974,530 A | 8/1976 | Lusch et al. |
| 4,097,940 A | 7/1978 | Tekulve et al. |

(Continued)

FOREIGN PATENT DOCUMENTS

| AU | 163976 | 7/1955 |
|---|---|---|
| DE | 12 88 744 B | 2/1969 |

(Continued)

OTHER PUBLICATIONS

European Search Report dated Apr. 4, 2008 for Application No. EP 07 25 0195, (8 pages).

(Continued)

*Primary Examiner* — William Kelleher
(74) *Attorney, Agent, or Firm* — Barnes & Thornburg LLP

(57) ABSTRACT

A patient support apparatus includes a frame and seat, thigh, and head sections coupled to the frame. A linkage is coupled to the head, seat, and thigh sections. The linkage has a first mode of operation in which the seat and thigh sections remain substantially parallel to each other as the head section is raised and lowered and the linkage has a second mode of operation in which the thigh section tilts relative to the seat section as the head section is raised and lowered. A handle is movable relative to the head section between a first position in which the linkage is in the first mode of operation and a second position in which the linkage is in the second mode of operation.

19 Claims, 12 Drawing Sheets

U.S. PATENT DOCUMENTS

| | | |
|---|---|---|
| 4,127,906 A | 12/1978 | Zur |
| 4,139,917 A | 2/1979 | Fenwick |
| 4,312,500 A | 1/1982 | Janssen |
| 4,371,996 A | 2/1983 | Nahum |
| 4,376,316 A | 3/1983 | Mercier et al. |
| 4,380,838 A | 4/1983 | Lutchansky |
| 4,403,357 A | 9/1983 | Degen |
| 4,406,027 A | 9/1983 | Bourda |
| 4,411,035 A | 10/1983 | Fenwick |
| D271,729 S | 12/1983 | Dodrill |
| 4,559,656 A | 12/1985 | Foster |
| 4,592,104 A | 6/1986 | Foster et al. |
| 4,637,652 A | 1/1987 | Bergenwall |
| 4,675,926 A | 6/1987 | Lindblom et al. |
| 4,754,508 A | 7/1988 | Nishiguchi |
| 4,894,876 A | 1/1990 | Fenwick |
| 4,937,900 A | 7/1990 | Bridges |
| 4,944,055 A | 7/1990 | Shainfeld |
| 5,072,463 A | 12/1991 | Willis |
| 5,105,486 A | 4/1992 | Peterson |
| 5,157,787 A | 10/1992 | Donnellan et al. |
| 5,245,718 A | 9/1993 | Krauska |
| 5,402,544 A | 4/1995 | Crawford et al. |
| 5,444,883 A | 8/1995 | Iura |
| RE35,201 E | 4/1996 | Krauska |
| 5,584,082 A | 12/1996 | Crawford et al. |
| 5,678,264 A | 10/1997 | Walker |
| 5,790,997 A | 8/1998 | Ruehl |
| 5,996,151 A | 12/1999 | Bartow et al. |
| 6,076,209 A | 6/2000 | Paul |
| 6,089,593 A | 7/2000 | Hanson et al. |
| 6,138,303 A | 10/2000 | Alvestad |
| 6,154,899 A | 12/2000 | Brooke et al. |
| 6,230,346 B1 | 5/2001 | Branson et al. |
| 6,247,753 B1 | 6/2001 | Alvestad |
| 6,296,261 B1 | 10/2001 | deGoma |
| 6,315,319 B1 | 11/2001 | Hanson et al. |
| 6,351,861 B1 | 3/2002 | Shows et al. |
| 6,494,538 B1 | 12/2002 | Alvestad |
| 6,565,112 B2 | 5/2003 | Hanson et al. |
| 6,643,873 B2 | 11/2003 | Heimbrock et al. |
| 6,679,556 B1 | 1/2004 | Alvestad |
| 6,694,549 B2 | 2/2004 | Perez et al. |
| 6,726,279 B1 | 4/2004 | Figel et al. |
| 6,839,926 B2 | 1/2005 | Heimbrock et al. |
| 6,846,042 B2 | 1/2005 | Hanson et al. |
| 6,907,631 B2 | 6/2005 | Heaton |
| 7,124,456 B2 | 10/2006 | Palmatier et al. |
| 8,069,513 B2 * | 12/2011 | Turner et al. .................. 5/618 |
| 2002/0152551 A1 | 10/2002 | Perez et al. |
| 2002/0157185 A1 | 10/2002 | Heimbrock et al. |
| 2005/0125899 A1 | 6/2005 | Hanson |
| 2006/0031990 A1 | 2/2006 | Palmatier et al. |
| 2006/0031991 A1 | 2/2006 | McDaniel et al. |
| 2006/0162077 A1 | 7/2006 | McDaniel et al. |
| 2007/0180621 A1 | 8/2007 | Turner et al. |

FOREIGN PATENT DOCUMENTS

| | | | |
|---|---|---|---|
| DE | 3444448 A1 | | 6/1986 |
| DE | 3615223 A1 | | 4/1987 |
| DE | 3618680 A1 | | 12/1987 |
| DE | 19654110 C1 | | 1/1998 |
| EP | 0 657 154 A2 | | 6/1995 |
| EP | 0 852 123 A1 | | 7/1998 |
| EP | 1 346 666 | | 9/2003 |
| EP | 1 350 449 | | 10/2003 |
| EP | 1 486 191 A1 | | 12/2004 |
| EP | 1 810 652 | | 1/2007 |
| FR | 2 555 426 | | 5/1985 |
| FR | 2 635 681 | | 3/1990 |
| FR | 2 711 521 | | 5/1995 |
| GB | 1 411 903 | A | 10/1975 |
| GB | 2 345 439 | A | 7/2000 |
| JP | 2001-511047 | A | 8/2001 |
| WO | 98/34575 A2 | | 8/1998 |
| WO | WO 03/057126 | | 7/2003 |

OTHER PUBLICATIONS

European Search Report dated Aug. 6, 2008 for Application No. EP 08 25 1082, (8 pages).

European Search Report dated May 16, 2011 for Application No. EP 10 19 3522, (3 pages).

European Search Report dated Apr. 12, 2011 for Application No. EP 10 19 3519, (3 pages.

Official action from related JP 2007-010836 dated Nov. 15, 2011 (with translation), 8 pages.

* cited by examiner

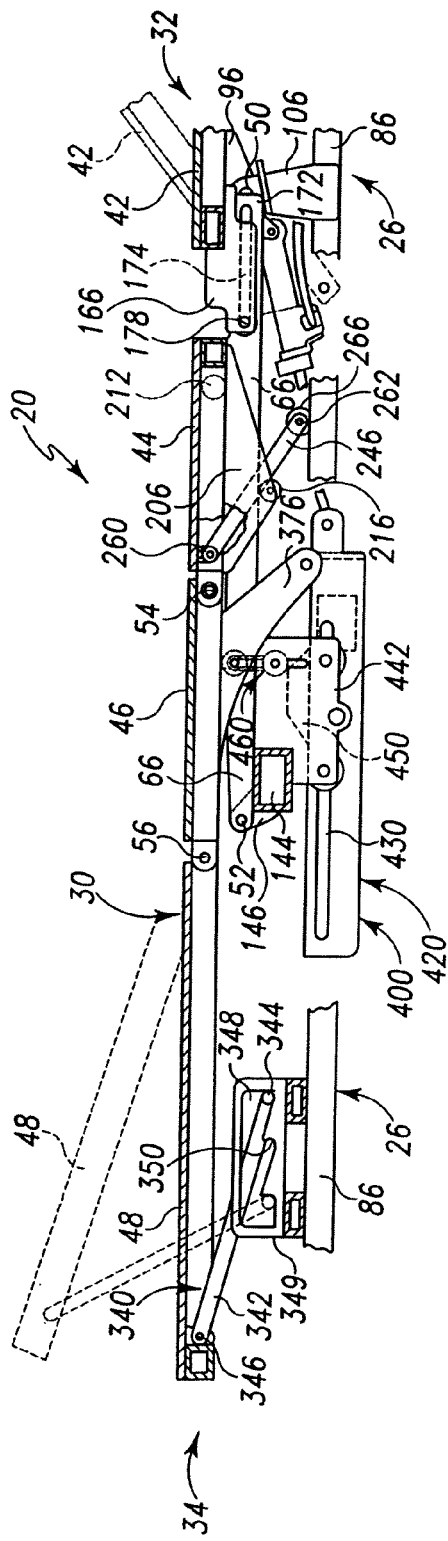
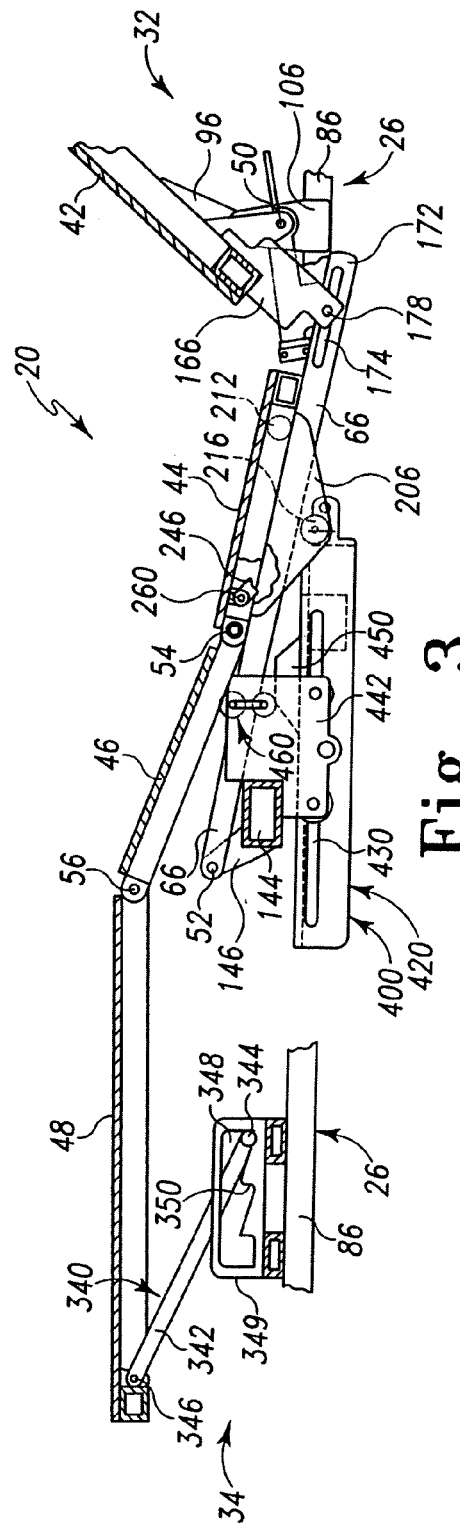

AUTO CONTOUR HANDLE APPARATUS

CROSS REFERENCE TO RELATED APPLICATIONS

This application is a continuation of U.S. application Ser. No. 11/622,069, filed Jan. 11, 2007, now U.S. Pat. No. 8,069,513, which claims the benefit of U.S. Provisional Patent Application No. 60/760,343, filed Jan. 19, 2006, and entitled "Procedural Stretcher," and U.S. Provisional Patent Application No. 60/804,227, filed Jun. 8, 2006, and entitled "Stretcher," the disclosures of each of which are hereby incorporated by reference herein.

BACKGROUND OF THE INVENTION

The present disclosure generally relates to a patient support apparatus, such as a hospital bed or a stretcher, having an articulated patient support deck. More particularly, the present disclosure relates to a patient support apparatus having an auto contour feature to raise the knees of a patient supported on the deck as a head section of the deck is raised.

If a patient's knees are not raised when the patient's head is raised, the patient has a tendency to migrate toward the foot end of the stretcher. A caregiver may have to reposition the patient back toward the head end of the stretcher, which can be difficult, especially when the patient is heavy. Some stretchers and hospital beds have an auto contour mechanism which causes a thigh section of the deck to raise when the head section is raised. There are some instances, however, when a caregiver may not want the thigh section to raise when the head section is raised. Stretchers often have one or more gas springs that aid a caregiver in lifting the head section of the deck and that lock the head section in a desired position. Even in stretchers with gas springs, raising the head section with a patient supported on the deck can be difficult for heavier patients.

Although the term "stretcher" is used throughout this disclosure, it is understood that the teachings of this disclosure may be incorporated into other types of patient support apparatuses, such as, for example, hospital beds, imaging tables, operating tables, and so on. The term "patient support apparatus," as used in this description and claims, therefore, shall be understood to include any type of patient support apparatus, such as, for example, a stretcher, a hospital bed, an imaging table, an operating table, and the like.

SUMMARY OF THE INVENTION

The present invention comprises an apparatus that has one or more of the features listed in the appended claims, or one or more of following features or combinations thereof, which alone or in any combination may comprise patentable subject matter:

According to the present disclosure, a patient support apparatus may include a frame, at least one drop rail coupled to the frame and tiltable relative to the frame, a seat section supported by the at least one drop rail to tilt therewith, a thigh section, a head section coupled to the frame and coupled to the at least one drop rail so that the at least one drop rail tilts as the head section is tilted, and a linkage coupled to the head section and coupled to the thigh section. The linkage may have a first mode of operation in which the seat and thigh sections remain substantially parallel as the at least one drop rail tilts. The linkage may have a second mode of operation in which the thigh section tilts relative to the seat section as the at least one drop rail tilts. The thigh section may be situated, at least in part, above the at least one drop rail.

The head section may be coupled to the frame for pivoting movement about a first axis. The at least one drop rail may be coupled to the frame for pivoting movement about a second axis. The thigh section may be coupled to the seat section for pivoting movement about a third axis located between the first and second axes. A foot section may be coupled to the thigh section for pivoting movement about a fourth axis. The second axis may be located generally beneath the fourth axis. The first, second, third, and fourth axes may extend laterally with respect to the frame and the deck.

The head section may be movable from a lowered position in which the head section is generally horizontal to a raised position through an intermediate position. The thigh section may be movable upwardly from a first position generally parallel with the at least one drop rail to a second position in which the thigh section is raised with respect to the at least one drop rail as the head section moves from the lowered position to the intermediate position. The thigh section may be movable downwardly relative to the at least one drop rail from the second position to the first position parallel with the at least one drop rail as the head section moves from the intermediate position to the raised position.

In some embodiments, the seat section may be fixed to the at least one drop rail. In other embodiments, the seat section may be supported by the at least one drop rail for translation along the at least one drop rail. The apparatus may include a link coupled to the frame and coupled to the seat section to move the seat section along the drop rail away from the head section as the at least one drop rail is tilted downwardly and to move the seat section along the drop rail toward the head section as the at least one drop rail is tilted upwardly.

The at least one drop rail may comprise a pair of laterally-spaced drop rails. Each drop rail may have a foot end coupled to the frame for pivoting movement such that each drop rail is movable between a first position generally parallel with the frame and a lowered second position. Each drop rail may have a head end including a longitudinally extending slot in which a laterally extending pin coupled to a foot end of the head section is received for translating movement. A roller may be coupled to the pin and each of the drop rails may have a top wall and two side walls extending downwardly from the top wall such that a downwardly opening channel is provided in each drop rail beneath the respective top wall and between the associated side walls. A roller may be coupled to each of the pins and situated within the corresponding channels. The rollers may contact the associated top walls of the respective drop rails to support the drop rails with respect to the head section.

The linkage may comprise a cam supported by the frame and a roller assembly contacting the thigh section and contacting the cam. The cam may be coupled to the head section so that, as the head section is raised and lowered, the cam moves along the frame. The cam may have a first portion along which the roller assembly moves to raise the thigh section as the head section moves from the lowered position to the intermediate position, and the cam may have a second portion along which the roller assembly moves to lower the thigh section as the head section moves from the intermediate position to the raised position. The second portion of the cam may be inclined with respect to the first portion.

The roller assembly may be coupled to the frame for movement in a direction generally perpendicular to a generally horizontal frame member of the frame. The roller assembly may include a top roller positioned to engage an underside of the thigh section and a bottom roller positioned to engage the cam. The linkage may comprise a lockable device, such as a spring clutch, including a housing coupled to the head section, a coil gripping spring received inside the housing, and a connecting rod. The connecting rod may have a first portion received inside the gripping spring and a second portion coupled to the cam. The spring clutch may be locked when the linkage is in the second mode so that the gripping spring constricts around the connecting rod to couple the head section to the cam so that the thigh section is initially raised and then lowered relative to the at least one drop rail as the head section is raised. The spring clutch may be released when the linkage is in the first mode so that the gripping spring loosens its grip on the connecting rod to decouple the head section from the cam so that the head section can be raised without also raising and lowering the thigh section relative to the at least one drop rail.

The apparatus may include at least one handle coupled to the head section and movable between a locking position in which the spring clutch is locked to couple the head section to the cam and a releasing position in which the spring clutch is released to decouple the head section from the cam. A bar may be coupled to the at least one handle for movement in a longitudinal direction. Movement of the at least one handle between the locking and releasing positions may result in movement of the bar between a first position closer to a foot end of the head section and a second position closer to a head end of the head section. A cable may be coupled to the bar and coupled to the spring clutch. The spring clutch may be normally locked. Movement of the bar from the first position to the second position may pull the cable to unlock the spring clutch to decouple the head section from the cam.

The head section may include a bottom panel having a pair of corner portions near its head end. The at least one handle may comprise a pair of handles coupled to the bottom panel adjacent the respective corner portions. The handles may be coupled together so that movement of one of the handles from its locking position to its releasing position results in corresponding movement of the other handle from its locking position to its releasing position. Each handle may include a cam portion. The cam portions may engage the bar to move the bar from the first position to the second position as the two handles move from their locking positions to their releasing positions.

The at least one handle may include a generally circular portion having a pair of notches corresponding to the two positions of the handle. A locking member may be coupled to the bottom panel of the head section. The locking member may be movable to a locking position in which a locking portion thereof is received in one of the two notches in the circular portion to prevent the handle from moving when the head section is raised. The locking member may be moved to a releasing position in which the locking portion is withdrawn from the associated notch to free the handle when the head section is in the lowered position. The locking member may be biased toward the locking position. A post may engage and move the locking member to the released position automatically as the head section moves to the lowered position.

The apparatus may include an actuator coupled to the head section and coupled to the frame. The actuator may be lockable to prevent tilting movement of the head section relative to the frame and the actuator may be releasable to allow pivoting movement of the head section relative to the frame. At least one head section release handle may be coupled to the bottom panel of the head section. Movement of the head section release handle from its locking position to its releasing position may release the actuator to permit tilting of the head section relative to the frame. In some embodiments, the at least one head section release handle may comprise a pair of head section release handles coupled to the bottom panel near respective corner portions thereof. Each of the release handles may be moved longitudinally, laterally, and diagonally, as well in as any intermediate direction therebetween, to release the actuator.

Additional features, which alone or in combination with any other feature(s), such as those listed above and those listed in the appended claims, may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which:

FIG. 2 is a side elevation view, with portions broken away, of the stretcher of FIG. 1 showing the head, seat, thigh and foot sections disposed horizontally;

FIG. 3 is a side elevation view, similar to FIG. 2, of the stretcher of FIG. 1 showing the head section raised to an intermediate position, the seat section dropped downwardly along with a drop rail, the thigh section raised relative to the seat section up off the drop rail, and the foot section having one end supported by the thigh section and the other end supported by a rocker arm;

DETAILED DESCRIPTION OF THE DRAWINGS

Figure 1:
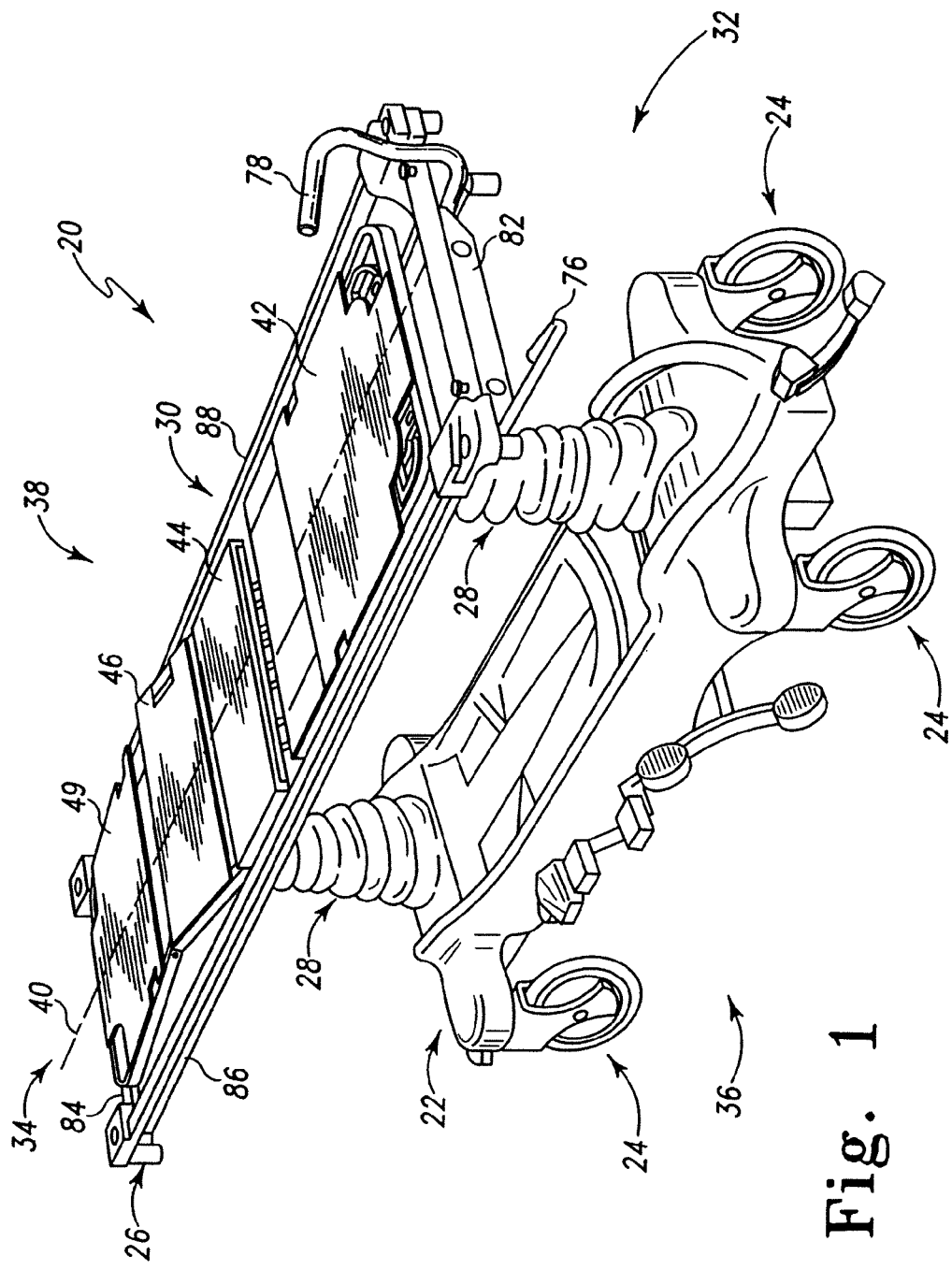
FIG. 1 is a perspective view of an illustrative stretcher showing a lower frame supported on casters, an upper frame supported above the lower frame, a deck supported by the upper frame, the deck having head, seat, thigh, and foot sections, a pair of push handles coupled to the upper frame near the head end, and a plurality of foot pedals coupled to the lower frame.

Referring to FIGS. 1-4, a patient support apparatus, such as a stretcher 20, includes a lower frame 22 supported on casters 24, an upper frame 26 coupled to the lower frame 22 by an elevation adjustment mechanism 28, a patient support deck 30 coupled to the upper frame 26, a head end 32, a foot end 34, an elongated left side 36, an elongated right side 38, and a longitudinal axis 40. A pair of push handles 76, 78 are coupled to the upper frame 26 near the head end 32 for movement between a lowered storage position (shown with respect to the left handle 76) and a raised use position (shown with respect to the right handle 78). For clarity of illustration, the stretcher 20 is shown without a pair of siderails on opposite sides 36, 38 of the upper frame 26.

As used in this description, the phrase "head end 32" will be used to denote the end of any referred-to object that is positioned to lie nearest the head end 32, and the phrase "foot end 34" will be used to denote the end of any referred-to object that is positioned to lie nearest the foot end 34. Likewise, the phrase "left side 36" will be used to denote the side of any referred-to object that is positioned to lie nearest the left side 36, and the phrase "right side 38" will be used to denote the side of any referred-to object that is positioned to lie nearest the right side 38.

As shown in FIGS. 1-4, the deck 30 includes longitudinally spaced and laterally extending head, seat, thigh and foot sections 42, 44, 46, 48. The head, seat, thigh and foot sections 42, 44, 46, 48 define an upwardly-facing support surface for supporting a mattress pad (not shown). The mattress pad, in turn, supports a patient (not shown). A foot end 34 of the head section 42 is coupled to the frame 26 for pivoting movement about a lateral first axis 50 shown in FIG. 5. Foot ends 34 of a pair of laterally spaced left and right drop rails 66, 68 are coupled to the frame 26 for pivoting movement about a lateral second axis 52, also shown in FIG. 5. The foot end 34 of the head section 42 is coupled to the head ends 32 of the left and right drop rails 66, 68 for translation along the drop rails 66, 68 so that the drop rails 66, 68 tilt downwardly as the head section 42 tilts upwardly as shown in FIGS. 2 and 3. The seat section 44 is supported on the drop rails 66, 68 for translation along the drop rails 66, 68. A head end 32 of the thigh section 46 is coupled to the seat section 44 for pivoting movement about a lateral third axis 54 located between the first and second axes 50, 52 as shown in FIG. 5. A head end 32 of the foot section 48 is coupled to the thigh section 46 for pivoting movement about a lateral fourth axis 56, also shown in FIG. 5. The fourth axis 56 is located generally above the second axis 52.

The frame 26 includes a pair of laterally extending head and foot end cross members 82, 84, which are longitudinally spaced apart and extend between longitudinally extending left and right side frame members 86, 88 as shown in FIG. 1. As shown in FIGS. 2-5, a pair of laterally-spaced flanges 96 extends downwardly from an underside of the head section 42 on a left side 36 thereof. The laterally-spaced flanges 96 are coupled by a transversely extending pivot pin 90 (FIG. 5) to a flange 106 (FIGS. 2-4) extending upwardly from the left frame member 86 of the frame 26. Likewise, a pair of laterally-spaced flanges 98 (FIG. 5) extend downwardly from the underside of the head section 42 on a right side 38 thereof. The laterally-spaced flanges 98 are coupled by a transversely extending pivot pin 92 to a flange (not shown) extending upwardly from the right frame member 88 of the frame 26. The transversely extending pivot pins 90, 92 are aligned and define the first axis 50 about which head section 42 pivots relative to frame 26.

As shown in FIG. 5, a lockable actuator, such as a gas spring 120, is coupled to the head section 42 and coupled to the frame 26 for aiding a caregiver in lifting the head section 42 of the deck 30 when a patient is supported on the deck 30. The gas spring 120 includes a housing 122 coupled to the head section 42, a piston (not shown) received inside the housing 122 and a piston rod 124 coupled to the piston and coupled to the frame 26. A pair of laterally spaced flanges 128 extends downwardly from the underside of the head section 42. The laterally-spaced flanges 128 are coupled by a laterally extending pivot pin 129 to a flange 132 that extends toward the head end 32 from the housing 122 of the gas spring 120 as shown in FIG. 5. The foot end 34 of the piston rod 124 is coupled for pivoting movement to a pair of laterally-spaced flanges 134 extending downwardly from a cross member 144 of the frame 26 in a region generally beneath the thigh section 46.

The gas spring 120 can be locked so that piston rod 124 is generally fixed relative to the housing 122 of the gas spring 120 and so that the piston rod 124 can neither extend out of the housing 122 nor retract into the housing 122, thereby preventing the head section 42 from pivoting relative to the frame 26. The gas spring 120 can also be released so that the piston rod 124 can extend out of the housing 122 or retract into the housing 122, thereby allowing the head section 42 to pivot relative to the frame 26, for example, to raise or lower the head section 42. The gas spring 120 includes a trigger plate 136 coupled to a plunger (not shown) extending out of the piston rod 124 near the foot end 34 thereof. The trigger plate 136 has a locking position in which the gas spring 120 is locked to prevent the head section 42 from pivoting relative to the frame 26. The trigger plate 136 has a releasing position in which the gas spring 120 is released allowing the head section 42 to pivot relative to the frame 26. The plunger is typically biased into an extended locking position so that the head section 42 is normally locked in place. When the trigger plate 136 moves from the locking position to the releasing position, it pushes the plunger further into the housing to unlock and release the gas spring. Although a lockable gas spring is used in the illustrated embodiment for locking the head section 42 relative to the frame 26, it is, however, within the scope of this disclosure as presently perceived to use any other actuator which serves as a suitable locking device that can be locked to prevent pivoting movement of the head section 42 and that can be released to allow pivoting movement of the head section 42.

As shown in FIG. 5, a foot end 34 of the left drop rail 66 is coupled to a pair of laterally-spaced flanges 146 extending upwardly from the cross member 144 of the frame 26 for pivoting movement about a transversely extending pin 150. Likewise, a foot end 34 of the right drop rail 68 is coupled to a pair of laterally-spaced flanges 148 extending upwardly from the cross member 144 of the frame 26 for pivoting movement about a transversely extending pin 152. The transversely extending pins 150, 152 are aligned and define the second axis 52. As shown in FIG. 5, the longitudinal position of the second axis 52 generally corresponds to the longitudinal position of the fourth axis 56 and the longitudinal position of the knees of a patient supported on the deck 30, although there is some amount of offset between axis 52 and axis 56 in the longitudinal direction in the illustrative embodiment.

As also shown in FIG. 5, a pair of laterally-spaced flanges 166 extend downwardly from an underside of the head section 42 on a left side 36 thereof. The laterally-spaced flanges 166 are configured to form a slot 170 for receiving a head end portion 172 of the left drop rail 66. Each of the drop rails 66, 68 is configured as a channel member having a top wall 173 and a pair of side walls 175 that extend downwardly from sides 36, 38 of top wall 173. Thus, each drop rail 66, 68 has a downwardly opening channel defined beneath the respective top wall 173 and between the associated side walls 175. In the region of a head end portion 172 of the left drop rail 66, the side walls 175 each have a longitudinally extending slot 174 (FIGS. 3 and 4) for receiving a laterally extending pin 178 that is coupled to the downwardly extending flanges 166 of the head section 42 as shown in FIGS. 3 and 4.

Likewise, a pair of laterally-spaced flanges 168 extend downwardly from the underside of the head section 42 on a right side 38 thereof. The laterally-spaced flanges 168 are configured to form a slot 180 for receiving a head end portion 182 of the right drop rail 68. In the region of a head end portion 182 of the right drop rail 68, the side walls 175 each have a longitudinally extending slot, similar to the slot 174, for receiving a transversely extending pin 188 (FIG. 5) coupled to the downwardly extending flanges 168 of the head section 42. The transversely extending pins 178, 188 are aligned and define a lateral fifth axis 58 shown in FIG. 5. The fifth axis 58 is located between the first axis 50 and the foot end 34 of the frame 26.

A roller 176 is coupled to pin 178 and is situated in the corresponding channel between side walls 175 of drop rail 66. Similarly, a roller 186 is coupled to pin 188 and is situated in the corresponding channel between side walls 175 of drop rail 68. The rollers 176, 186 contact the associated top walls 173 of the respective drop rails 66, 68 to support the drop rails 66, 68 with respect to the head section. Spacers or washers 177 are provided between flanges 166 and side walls 175 of drop rail 66. Likewise, spacers or washers 187 are provided between flanges 168 and side walls 175 of drop rail 68. The spacers 177, 187 and rollers 176, 186 are made of a plastic material, whereas the drop rails 66, 68, pins 178, 188, and flanges 166, 168 are made of metal.

Figure 4:
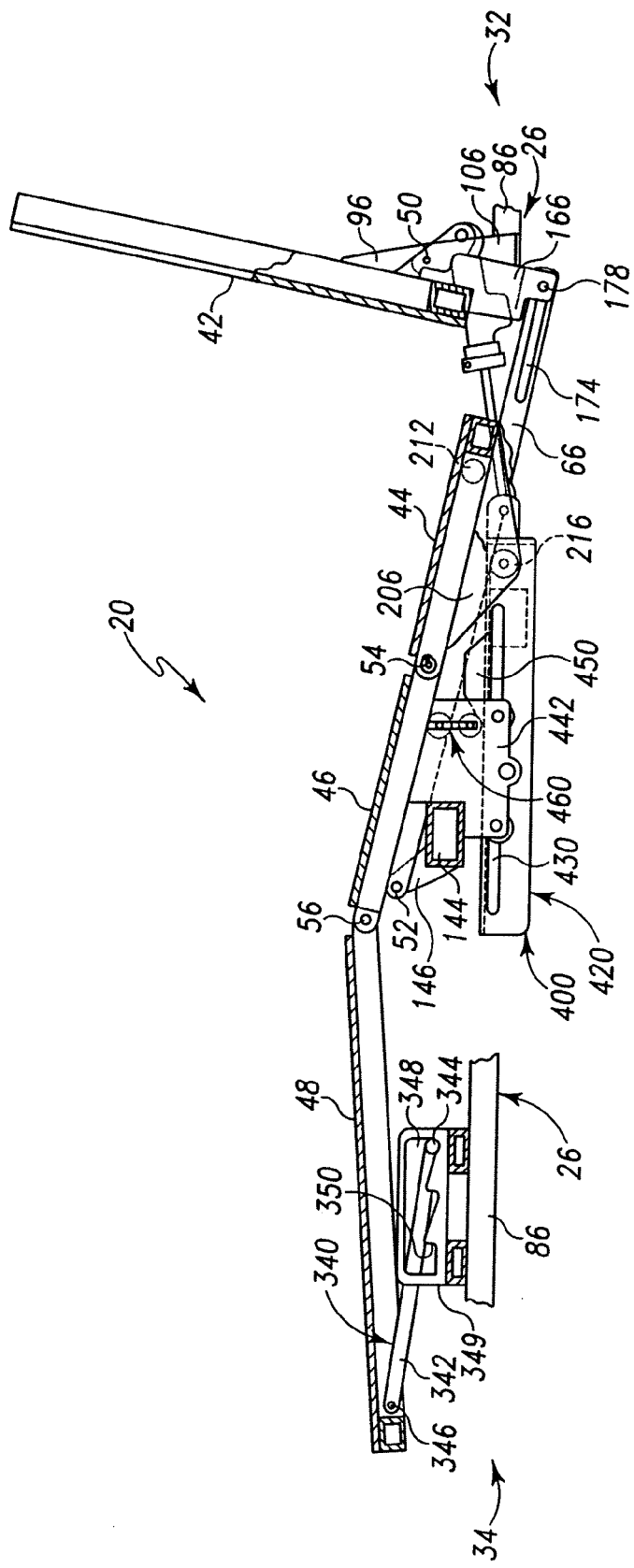
FIG. 4 is a side elevation view, similar to FIGS. 2 and 3, of the stretcher of FIG. 1 showing the head section raised to a near upright position with the thigh section lowered back down relative to the drop rail to be in alignment with the seat section.
Figure 5:
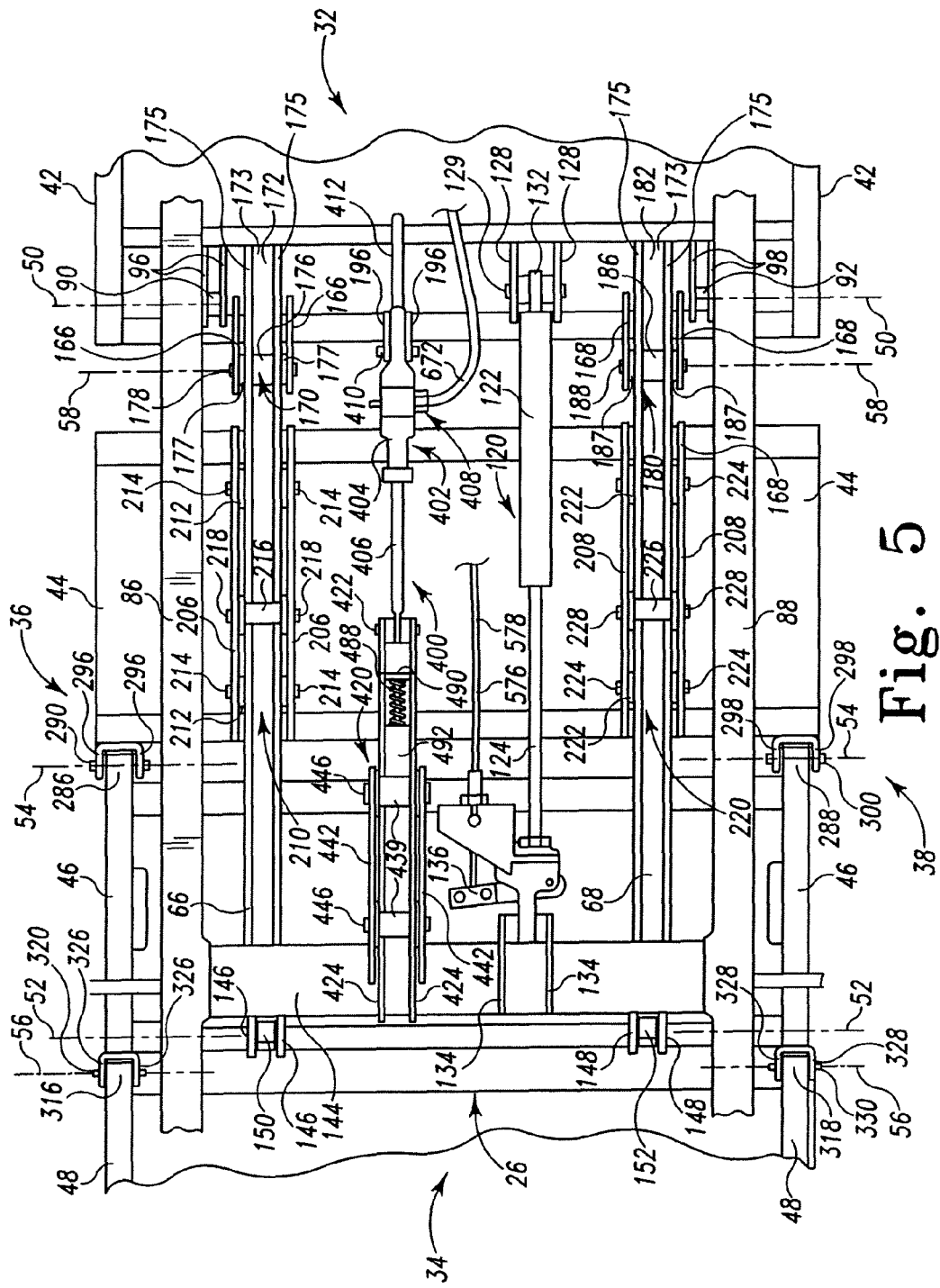
FIG. 5 is a bottom plan view of a portion of the stretcher of FIG. 1 showing a gas spring coupled to the head section and coupled to the upper frame, a spring clutch coupled to the head section and coupled to an elongate cam bracket carrying a cam, and a pair of drop rails coupled to the upper frame and coupled to the head section.

As shown in FIGS. 2-4, as the head end 32 of the head section 42 is raised about the pivot axis 50, the foot end 34 of the head section 42 is lowered. As the foot end 34 of the head section 42 is lowered, the pins 178, 188 carried by the flanges 166, 168 at the foot end 34 of the head section 42 move downwardly thereby lowering the head end 32 of the drop rails 66, 68, causing the drop rails 66, 68 to pivot downwardly about the pivot axis 52. As the head section 42 moves from its horizontal position shown in FIG. 2 to its upright position shown in FIG. 4 (about 80 degrees relative to horizontal), the pins 178, 188 carried by the flanges 166, 168 at the foot end 34 of the head section 42 move in the associated longitudinally extending slots 174 from their positions closer to the foot end 34 to their positions closer to the head end 32.

As shown in FIG. 5, a pair of laterally spaced flanges 206 extend downwardly from an underside of the seat section 44 on a left side 36 thereof. The laterally spaced flanges 206 are configured to form a slot 210 for receiving the left drop rail 66. Two top rollers 212 are rotatably coupled to the downwardly extending flanges 206 by associated laterally extending pins 214. The top rollers 212 ride on top wall 173 of the left drop rail 66. A bottom roller 216 is rotatably coupled to the downwardly extending flanges 206 by a laterally extending pin 218. The bottom roller 216 is located beneath the bottom edges of side walls 175 of the left drop rail 66. Likewise, a pair of laterally spaced flanges 208 extend downwardly from the underside of the seat section 44 on a right side 38 thereof. The laterally spaced flanges 208 are configured to form a slot 220 for receiving the right drop rail 68. Two top rollers 222 are rotatably coupled to the downwardly extending flanges 208 by associated transversely extending pins 224. The top rollers 222 ride on top wall 173 of the right drop rail 68. A bottom roller 226 is rotatably coupled to the downwardly extending flanges 208 by a transversely extending pin 228. The bottom roller 226 is located beneath the bottom edges of side walls 175 of the right drop rail 66.

Thus, the four top rollers 212, 222 and the associated pins 214, 224, two on each side, support the seat section 44 on the drop rails 66, 68 for translation therealong. The bottom rollers 216, 226 and the associated pins 218, 228 prevent seat section 44 from being lifted upwardly off of the drop rails 66, 68 thereby, securing the seat section 44 to the drop rails 66, 68. The top and bottom rollers 212, 216, 222, 226 are spool-shaped and, therefore, have enlarged rim portions to keep the rollers 212, 216, 222, 226 centered relative to the associated drop rails 66, 68. That is, the rim portions of rollers 212, 216, 222, 226 define grooves in which rails 66, 68 are received. These rim portions also serve as spacers to prevent side walls 175 of rails 66, 68 from contacting flanges 206, 208. Rollers 212, 216, 222, 226 are made of a plastic material, whereas rails 66, 68, pins 214, 218, 224, 228, and flanges 206, 208 are made of metal.

As shown in FIG. 2, left and right links 246 are pivotably coupled to the seat section 44 and are pivotably coupled to the frame 26. The coupling points between links 246 and seat section 44 and between links 246 and frame 26 are positioned so that the seat section 44 is pushed toward the foot end 34 of stretcher 20 as the head section 42 is raised and the drop rails 66, 68 are lowered. As the seat section 44 is pushed toward the foot end 34, the thigh section 46 is also pushed toward the foot end 34 of the stretcher 20 resulting in articulation of thigh section 46 relative to foot section 48 as shown in FIG. 3. The foot ends 34 of the links 246 are pivotally coupled to the seat section 44 by respective laterally extending pins 260. The head ends 32 of the links 246 are pivotally coupled to flanges 266 (FIG. 2) extending upwardly from the frame members 86, 88 of the frame 26 by respective laterally extending pins 262. As the head section 42 tilts upwardly from the horizontal position shown in FIG. 2 to the upright position shown in FIG. 4, the drop rails 66, 68 tilt downwardly from the horizontal position shown in FIG. 2 to the lowered position shown in FIG. 4. As the drop rails 66, 68 tilt downwardly, the links 246 also tilt or pivot downwardly about pins 262 to push the seat section 44 along the drop rails 66, 68 toward the foot end 34 of the drop rails 66, 68.

As shown in FIG. 5, the head ends 32 of frame members 286, 288 of thigh section 46 extend toward the seat section 44 from left and right sides 36, 38 of the thigh section 44. Frame member 286 is pivotally coupled by a laterally extending pin 290 to a pair of laterally spaced flanges 296 extending toward the foot end 34 of stretcher 20 from a left side 36 of the seat section 44. Likewise, frame member 288 is pivotally coupled by a laterally extending pin 300 to a pair of laterally spaced flanges 298 extending toward the foot end 34 of stretcher 20 from a right side 38 of the seat section 44. The laterally extending pins 290, 300 are aligned and define the third axis 54. The head ends 32 of frame members 316, 318 of foot section 48 extend toward the thigh section 46 from left and right sides 36, 38 of the foot section 48. Frame member 316 is pivotally coupled by a laterally extending pin 320 to a pair of laterally spaced flanges 326 extending toward the foot end 34 of stretcher 20 from the left side 36 of the thigh section 44. Likewise, frame member 318 is pivotally coupled by a laterally extending pin 330 to a pair of laterally spaced flanges 328 extending toward the foot end 34 of stretcher 20 from a left side 36 of the thigh section 44. The transversely extending pins 320, 330 are aligned and define the fourth axis 56.

As shown in FIGS. 2-4, the foot end 34 of the foot section 48 is pivotally coupled to the frame 26 by a generally U-shaped rocker frame 340. When the thigh section 46 is raised as shown in FIG. 3, the foot section 48 is raised therewith to lift the knees of the patient supported on the deck 30. The rocker frame 80 includes a pair of laterally spaced members 342 joined by a horizontal laterally extending member 344. Upper ends of the members 342 are pivotally coupled to the foot section 48 near the foot end 34 thereof by associated transversely extending pins 346. The opposite end regions of the member 344 are configured to be received in a pair of laterally spaced longitudinally extending slots 348 formed in respective flanges 349 that extend upwardly from frame members 86, 88 of frame 26. The slots 348 include a plurality of notches 350 along the lower edges thereof for releasably receiving the transversely extending member 344. The transversely extending member 344 is manually adjustable along the slots 348 to lift the foot section 48 to various positions of elevation. The closer the transversely extending member 344 to the foot end 34, the higher the elevation of the foot end 34 of the foot section 48.

Figure 6:
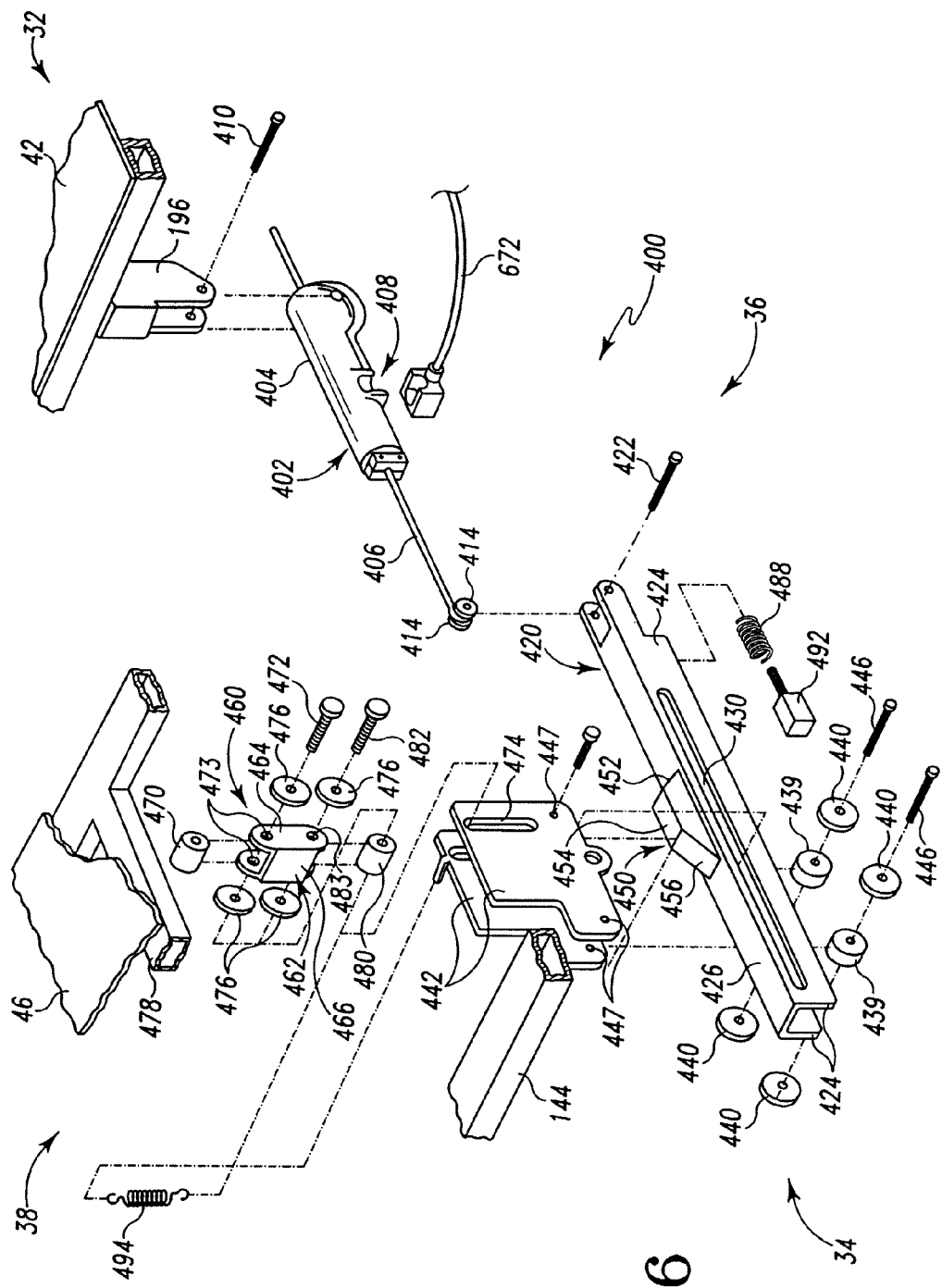
FIG. 6 is an exploded perspective view of an auto contour mechanism of the stretcher and portions of the head and thigh sections showing a pair of flanges extending downwardly from the head section, the spring clutch below the downwardly extending flanges, the cam bracket beneath a connecting rod of the spring clutch, and a roller assembly above a cam on the cam bracket and beneath the thigh section.
Figure 15:
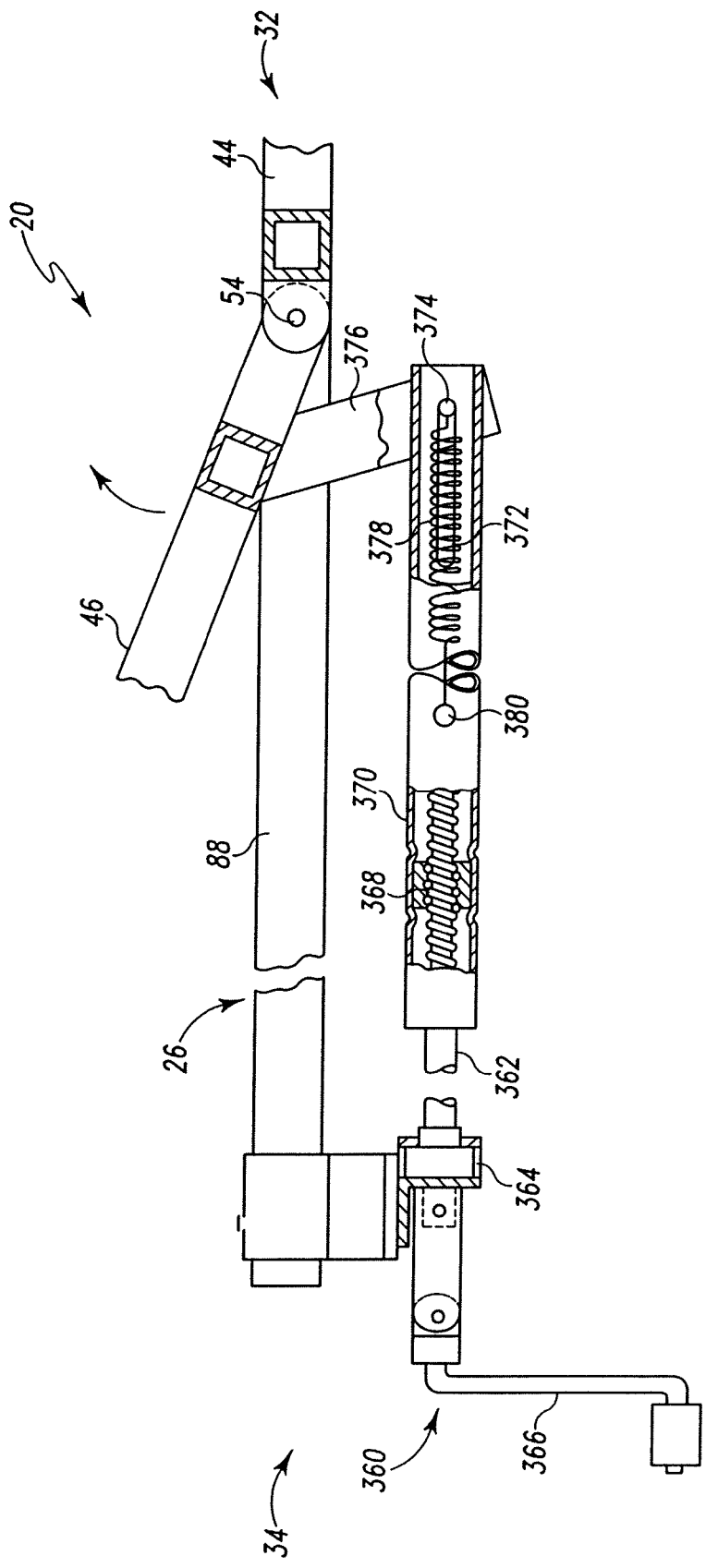
FIG. 15 is a side elevation view showing a knee crank mechanism for manually raising and lowering the thigh section independently of head section and the auto contour mechanism.

As shown in FIG. 15, the stretcher 20 includes a knee crank mechanism 360 to manually raise and lower the thigh section 46 independently of an auto contour mechanism 400 shown, for example, in FIG. 6. The knee crank mechanism includes a longitudinally extending ball screw 362 rotatably mounted to the frame 26. The foot end 34 of the ball screw 362 is supported by a bearing assembly 364 coupled to the frame 26. As a crank 366 coupled to the ball screw 362 is turned, the ball screw 362 threads into or out of a nut 368 fixed to a tube 370 to lengthen or shorten the distance between the head end 32 of the tube 370 and the foot end 34 of the ball screw 362. The head end 32 of the tube 370 includes a longitudinally extending slot 372 for receiving a laterally extending pin 374 coupled to a pair of laterally spaced flanges 376 extending downwardly from the underside of the thigh section 46. The crank 366 can be turned in a clockwise direction to raise the thigh section 46 independently of the auto contour mechanism 400 as shown, for example, in FIG. 1 in which head section 42 is in the lowered position but thigh section 46 is lifted slightly. Likewise, the crank 366 can be turned in a counterclockwise direction to lower the thigh section 46 independently of the auto contour mechanism 400. The longitudinally extending slot 372 in the tube 370 is sufficiently long to allow the auto contour mechanism 400 to raise the thigh section 46 to about a 30 degree angle independently of the knee crank mechanism 360. An illustrative knee crank mechanism is disclosed in U.S. Pat. No. 6,839,926, entitled "Patient Support Apparatus Having Auto Contour," which is hereby incorporated by reference herein.

Figure 14:
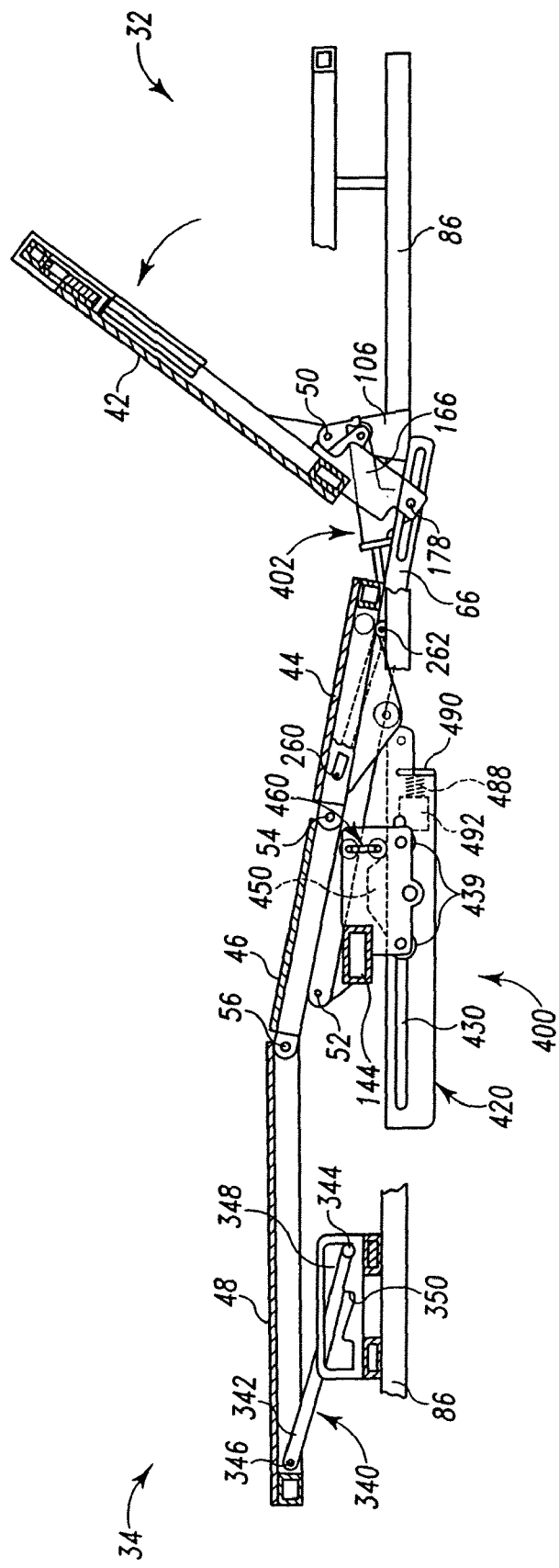
FIG. 14 is a side elevation view corresponding to FIG. 3, but with the auto contour mechanism in the "off" mode such that the seat section and the thigh section remain generally coplanar when the head section is in the intermediate position.

The auto contour mechanism 400 (sometimes referred to herein as "linkage 400"), shown, for example, in FIG. 6, is coupled to the head section 42 and coupled to the thigh section 46. Linkage 400 is operable in a first mode (FIGS. 2-4) to initially raise and then lower the thigh section 46 relative to drop rails 66, 68 as the head section 42 is raised from the horizontal position shown in FIG. 2 to the near upright position (about 80 degrees to horizontal) shown in FIG. 4 through an intermediate position (about 50 degrees to horizontal) shown in FIG. 3. In a second mode (FIG. 14) of operation, linkage 400 does not raise and lower the thigh section 46 relative to the drop rails 66, 68. However, it will be appreciated that, regardless of whether the linkage 400 is in the first mode or second mode of operation, the drop rails 66, 68 still tilt as the head section tilts as shown in FIG. 14.

Referring to FIGS. 2-7 in general and FIG. 6 in particular, the linkage 400 includes a lockable device 402, such as a spring clutch (e.g., a MECHLOC® device), that is lockable to place linkage 400 in the first mode of operation and that is unlockable or releasable to place linkage 400 in the second mode of operation. Device 402 is sometimes referred to herein as spring clutch 402. However, in the claims, the term "lockable device" is not intended to be limited to a spring clutch, but rather, is intended to mean all types of suitable devices that lock and unlock. The spring clutch 402 includes a housing 404, a gripping spring (not shown) inside the housing 404, a connecting rod 406, and a trigger plate 408. When the trigger plate 408 is in a releasing position, the spring clutch 402 is released or disengaged so that the gripping spring loosens its grip on the connecting rod 406 allowing the connecting rod 406 to slide relative to the clutch housing 404. When the trigger plate 408 is in a locking position, the spring clutch 402 is locked or engaged so that the gripping spring constricts around the connecting rod 406 to prevent the connecting rod 406 from sliding relative to the clutch housing 404. In the illustrated embodiment, the spring clutch 402 is normally locked.

A pair of laterally-spaced flanges 196 extend downwardly from the underside of the head section 42 on the left side 36 thereof as shown in FIGS. 5 and 6. The housing 404 is coupled to the downwardly extending flanges 196 for pivoting movement about a laterally extending pin 410. A portion 412 of the connecting rod 406 near its head end 32 is slidably received inside the gripping spring. The foot end 34 of the connecting rod 406 is pivotally coupled by a laterally extending pin 422 to a head end 32 of a longitudinally extending cam bracket 420 of the linkage 400. Spacers 414 are used to keep the connecting rod 406 centered relative to the cam bracket 420.

Figure 7:
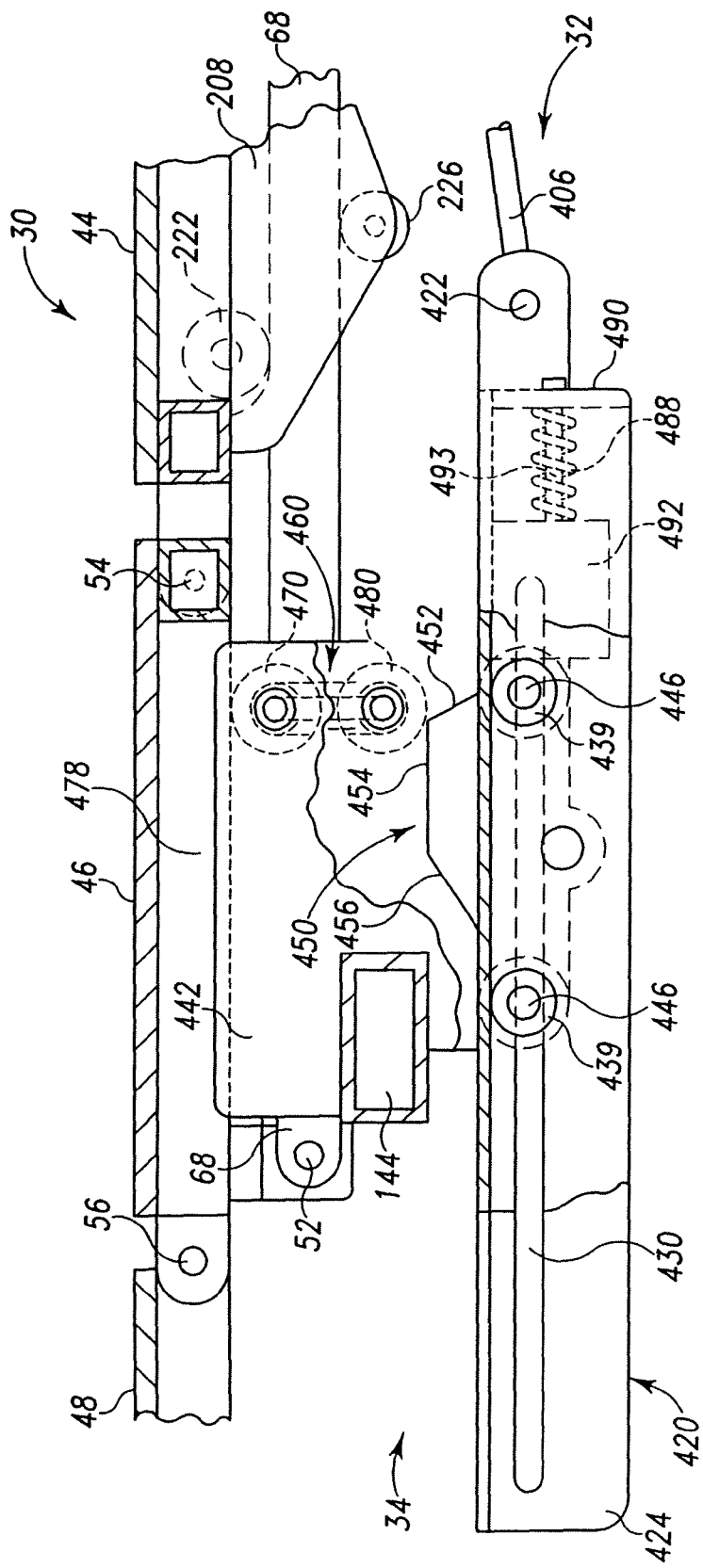
FIG. 7 is a side elevation view, with portions broken away, showing a roller bracket coupled to the upper frame, the cam bracket supported on rollers carried by the roller bracket, and the roller assembly having a top roller engaging an underside of the thigh section and having a bottom roller riding the cam.

Referring to FIGS. 6-7, the illustrative cam bracket 420 is a generally rectangular-shaped box or channel member with a pair of laterally-spaced longitudinally extending vertical plates or side walls 424 and a top plate or wall 426 extending therebetween. A foot end portion 428 of each plate 424 has a longitudinally extending slot 430. A pair of laterally spaced vertical flanges 442 are fixedly coupled to the cross member 144 of the upper frame 26. The cam bracket 420 is supported by a pair of rollers 439 that are rotatably coupled to transversely extending pins 446. Pins 446 extend through the longitudinally extending slots 430 in the cam bracket 420 and through associated apertures 447 provided in flanges 442. The end portions of the pins 446 are coupled to the vertical flanges 442 and retain cam bracket 420 in an orientation generally parallel with frame members 86, 88 of frame 26. Spacers 440 are used to keep the cam bracket 420 centered relative to the flanges 442. Rollers 439 and spacers 440 are made of a plastic material, whereas cam bracket 420 and flanges 442 are made of a metal material in the illustrative embodiment. A cam 450 of the linkage 400 is mounted on an upwardly-facing surface of the top plate 426. The cam 450 has an inclined portion 452 near its head end 32 that is relatively steep, an intermediate straight portion 454 that is generally horizontal, and an inclined portion 456 near its foot end 34 that is not so steep.

When the head section 42 is raised while the spring clutch 402 is locked, the downwardly extending flanges 196 of the head section 42 cause the housing 404 of the spring clutch 402 to move toward the head end 32 of the frame 26 as shown in FIGS. 2-4. This, in turn, causes the connecting rod 406 to move toward the head end 32 of stretcher, which causes the cam bracket 420 and the cam 450 mounted thereon also to move toward the head end 32 as shown in FIGS. 2-4. When the head section 42 is lowered while the spring clutch 402 is locked, the sequence is reversed. Thus, when the head section 42 is lowered, the clutch housing 404, the connecting rod 406, the cam bracket 420, and the cam 450 all move toward the foot end 34 of stretcher 20. When the head section 42 is raised while the spring clutch 402 is unlocked as shown in FIG. 14, the downwardly extending flanges 196 of the head section 42 still cause the clutch housing 404 to move toward the head end 32. However, the connecting rod 406, the cam bracket 420, and the cam 450 do not move toward the head end 32 but rather, the housing 404 and the clutch spring inside housing 404 slide upon rod 406.

As shown in FIGS. 6-7, the linkage 400 includes a roller assembly 460. The roller assembly 460 is coupled to the laterally spaced flanges 442 of the frame 26 for movement in generally upward and downward vertical directions. The roller assembly 460 includes a bracket 462 comprising a pair of laterally spaced vertical plates 464 and an end plate 466 extending therebetween. A top roller 470 is mounted to the laterally spaced plates 464 by a laterally extending pin 472 that extends through the oppositely disposed openings 473 in the laterally spaced plates 464 and then extends through the oppositely disposed vertically extending slots 474 in the laterally spaced flanges 442. Likewise, a bottom roller 480 is mounted to the laterally spaced plates 464 by a laterally extending pin 482 that extends through the oppositely disposed openings 483 in the laterally spaced plates 464 and then extends through the oppositely disposed vertically extending slots 474 in the laterally spaced flanges 442. Spacers 476 are used to keep the bracket 462 from contacting flanges 442 during upward and downward movement of roller assembly 460. Bracket 462 and pins 472, 482 are made of a metal material whereas rollers 470, 480 and spacers 476 are made of a plastic material.

As shown in FIGS. 6-7, the top roller 470 is positioned to engage the underside of a longitudinally extending member 478 of the thigh section 46. The bottom roller 480 is configured to engage the upper surface of the cam 450. As the head section 42 moves from its horizontal position shown in FIG. 2 to its intermediate position shown in FIG. 3 while the spring clutch 402 is locked, the cam 450 mounted on the cam bracket 420 moves toward the head end 32 from its position shown in FIG. 2 to its position shown in FIG. 3. As the cam 450 moves toward the head end 32 from its position shown in FIG. 2 to its position shown in FIG. 3, the bottom roller 480 rides along the straight portion 454 of the cam 450 to tilt the thigh section 46 upwardly about its pivot axis 54. The thigh section 46 tilts upwardly because the pivot axis 54 of the thigh section 46 relative to the seat section 44 is lowered as the drop rails 66, 68 tilt downwardly from their respective horizontal positions shown in FIG. 2 to their respective intermediate positions shown in FIG. 3. The bottom roller 480 arrives at the junction of the straight and inclined portions 454, 456 of cam 450 as the head section 42 arrives at the intermediate position as shown in FIG. 3.

As the head section 42 moves from the intermediate position shown in FIG. 3 to the near upright position shown in FIG. 4 while the spring clutch 402 is locked, the cam 450 mounted on the cam bracket 420 moves toward the head end 32 from the position shown in FIG. 3 to the position shown in FIG. 4. As the cam 450 moves toward the head end 32 from the position shown in FIG. 3 to the position shown in FIG. 4, the bottom roller 480 rides along the not-so-steep inclined portion 456 of the cam 450 to tilt the thigh section 46 downwardly to a position substantially coplanar with the seat section 44 as shown in FIG. 4. The thigh section 46 tilts downwardly because the roller assembly 460 that supports the thigh section 46 is lowered from the position shown in FIG. 3 to the position shown in FIG. 4.

When in the first mode of operation, the linkage 400 not only raises the thigh section 46 to prevent a patient from sliding toward the foot end 34 of the stretcher 20 when the head section 42 is raised from the lowered position to the intermediate position, but it also allows the head section 42 to be raised to a near upright position shown in FIG. 4 for chest x-rays by lowering the thigh section 46 back down relative to the drop rails 66, 68 to prevent the patient's legs and torso from folding together too much. Although a spring clutch 402 is used in the illustrated embodiment, it is within the scope of the invention to include any suitable lockable device that can be locked to prevent movement of the lockable device, and that can be released to allow extension and retraction of the lockable device. Thus, the term "spring clutch" as used in this specification and in the claims includes any suitable lockable device that can be engaged to couple the movement of the head section 42 to the cam 450, and that can be disengaged to decouple the movement of the head section 42 from the cam 450. In the illustrated embodiment, the spring clutch 402 is normally locked to couple the movement of the head section 42 to the cam bracket 420 to initially raise and then lower the thigh section 46 as the head section 42 is raised from the horizontal position shown in FIG. 2 to the near upright position shown in FIG. 4.

Figure 8:
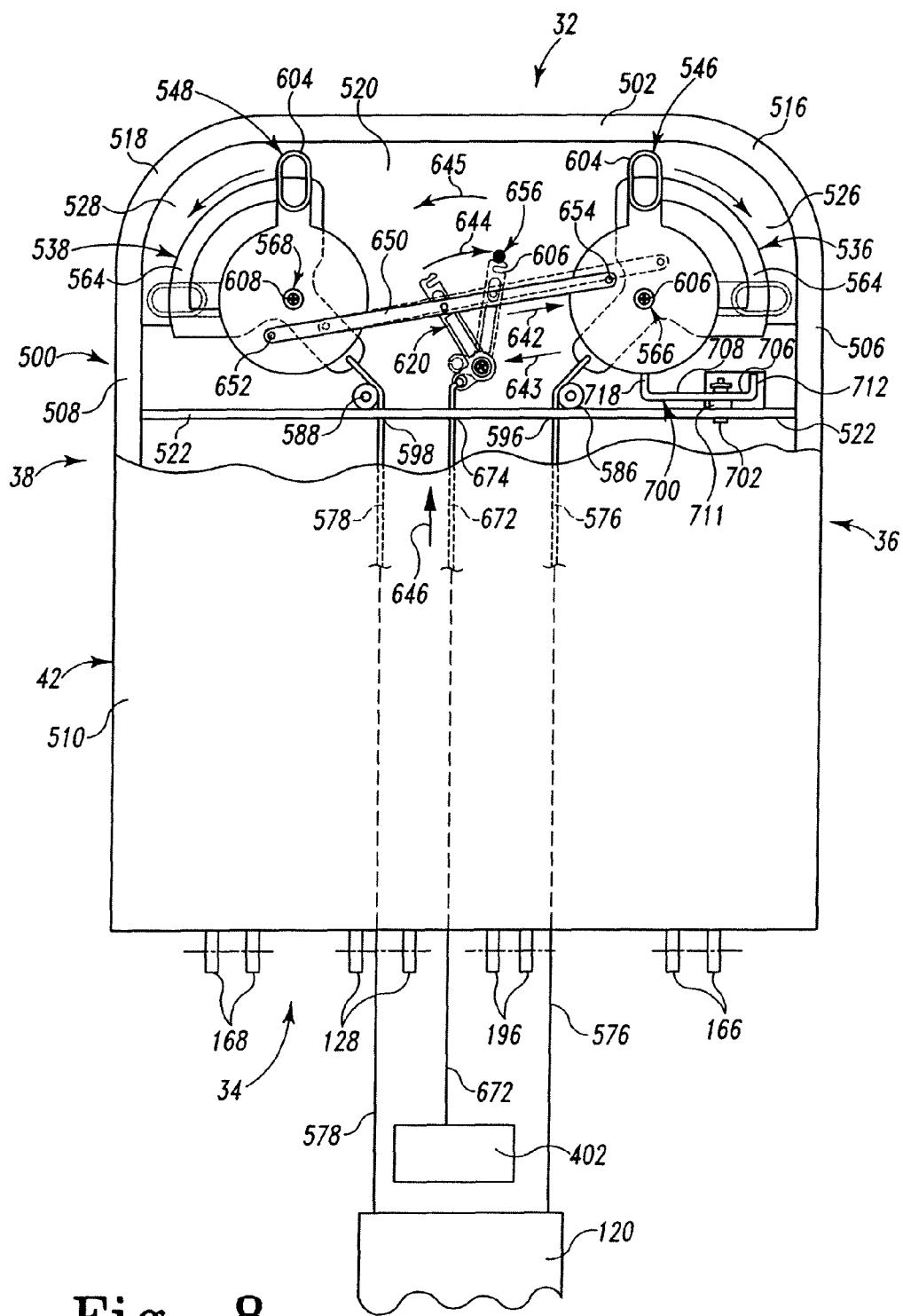
FIG. 8 is a top plan view, with portions broken away, of the head section showing the head section frame, a pair of auto contour on/off handles situated near corners of the frame, a pair of head section release handles underlying the on/off handles, a release bar coupled to the two on/off handles, a cable coupling the release bar to the spring clutch (shown diagrammatically), two cables coupling the release handles to a gas spring (shown diagrammatically), two rollers for guiding the two cables, and an auto contour lockout lever to the right of the rollers.
Figure 9:
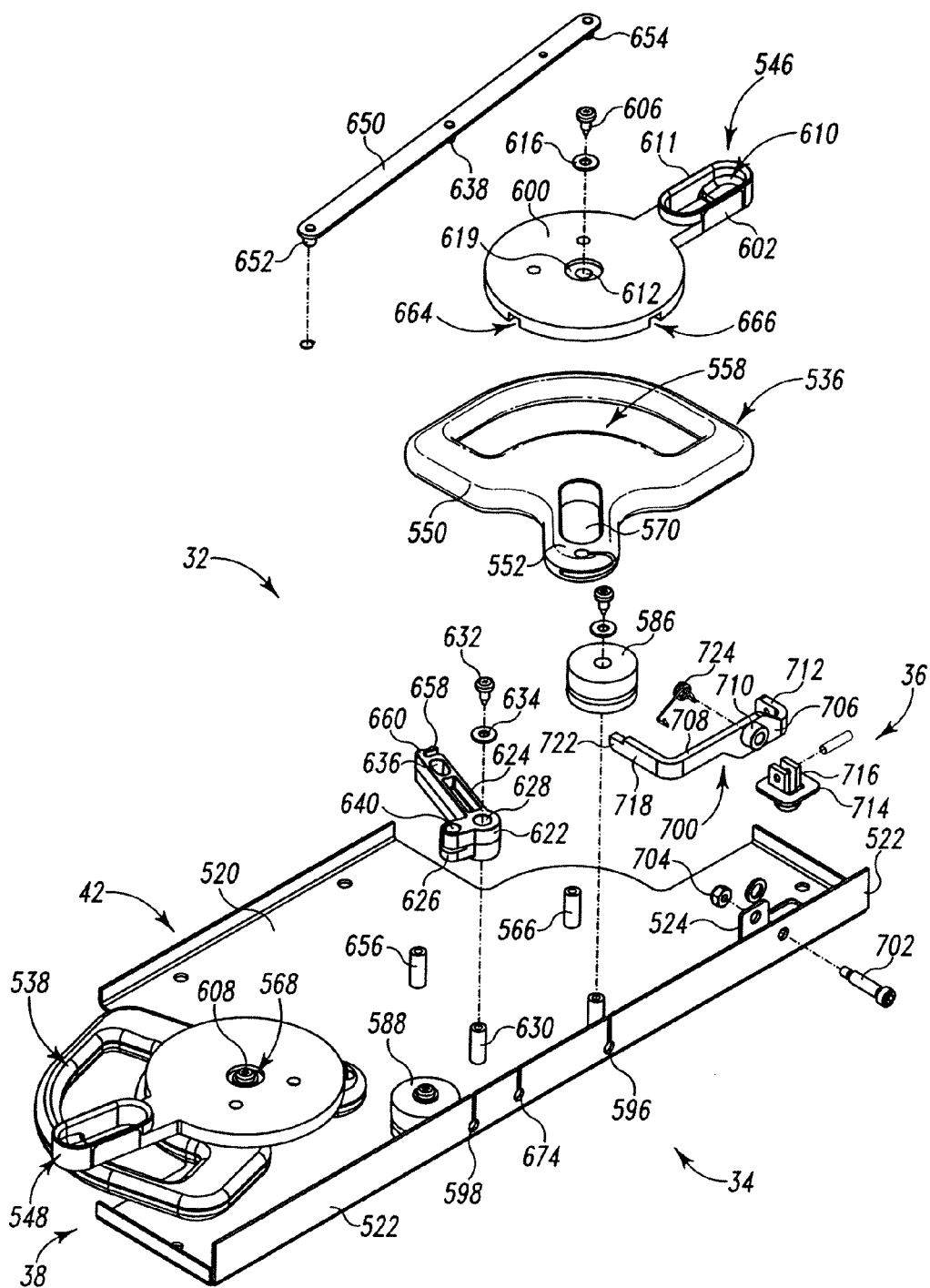
FIG. 9 is an exploded perspective view, with portions broken away, of the head section showing the head section frame, the auto contour on/off handles, the head section release handles, the laterally extending release bar, the three cables, and the auto contour lockout lever.

As shown in FIGS. 8 and 9, the head section 42 includes a tubular frame 500 and generally rectangular top and bottom panels 510, 520 attached to the frame 500 on top and bottom sides thereof by suitable fasteners (not shown). The tubular frame 500 has a head end strut 502, a pair of side struts 506, 508, and rounded corner portions 516, 518. Both the top and bottom panels 510, 520 have cutouts 526, 528 near the respective corner portions 516, 518 of the frame 500. A pair of head section release handles 536, 538 and a pair of auto contour on/off handles 546, 548 are mounted on the bottom panel 514 near the cutouts 526, 528 so that a caregiver standing near the head end 32 of the stretcher 20 has access to the head section release handles 536, 538 and the auto contour on/off handles 546, 548 through the cutouts 526, 528 from both the top side, as well as the bottom side, of the head section 42.

Figure 10:
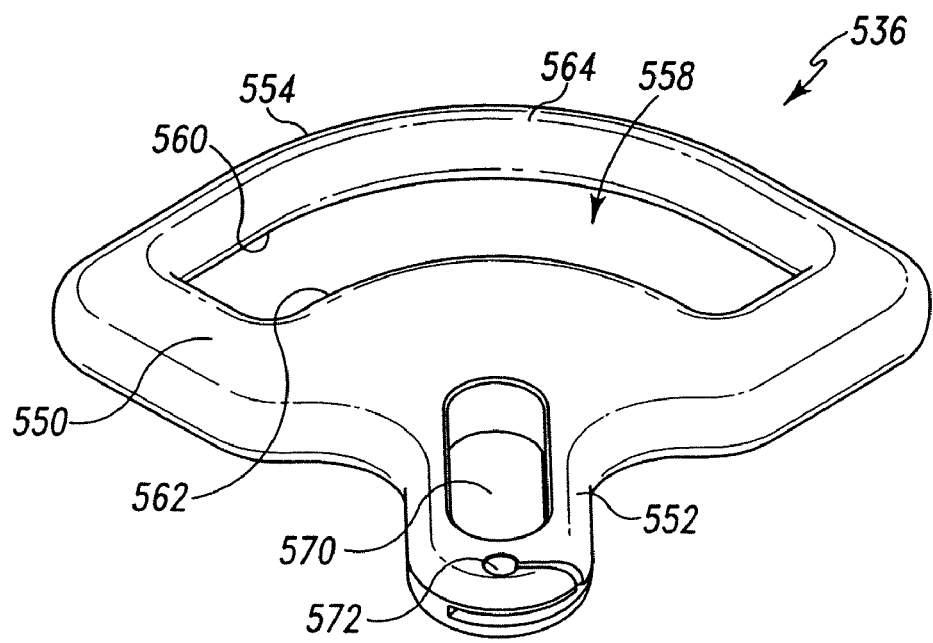
FIG. 10 is a perspective view of one of the head section release handles.

As shown in FIG. 10, each head section release handle 536, 538 has a generally flat pie-shaped body portion 550 and a leg portion 552 that extends outwardly from the body portion 550. The body portion 550 has an outwardly-facing edge 554 that has generally the same arcuate profile as the associated rounded corner portion 516, 518. The body portion 550 has an arcuate slot 558 defined by a pair of arcuate edges 560, 562 that are also generally parallel to the outwardly-facing edge 554. The arcuate slots 558 in the head section release handles 536, 538 provide handles 536, 538 with grip portions 564 near the associated corner portions 516, 518. The leg portions 552 of the head section release handles 536, 538 each have elongate slots 570. A pair of mounting pins 566, 568 extend upwardly from the bottom panel 520 near the respective corner portions 516, 518 as shown in FIGS. 8 and 9. The mounting pins 566, 568 extend upwardly through the elongate slots 570 in the associated head section release handles 536, 538.

Figure 11:
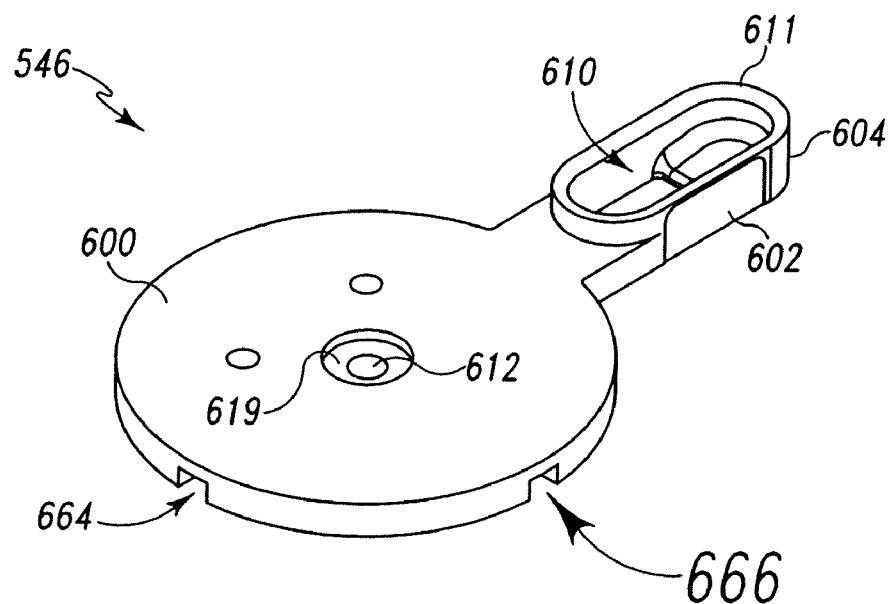
FIG. 11 is a bottom perspective view of one of the auto contour on/off handles showing a generally oval-shaped cam mounted on its underside.

As shown in FIG. 11, each auto contour on/off handle 546, 548 includes a generally flat circular body portion 600 and a handle portion 602 that extends outwardly from the circular body portion 600. The handle portion 602 of each auto contour on/off handle 546, 548 has an elongate slot 610 and an oval-shaped flange 611 that extends upwardly from an outer perimeter of the elongate slot 610. The handle portions 602 of the auto contour on/off handles 546, 548 form grip portions 604 near the associated corner portion 516, 518. The circular body portion 600 of each auto contour on/off handle 546 has a central opening 612 for receiving an associated mounting pin 566, 568. As shown in FIGS. 8 and 9, the mounting pins 566, 568 extend through the elongate slots 570 in the respective head section release handles 536, 538 and through the central openings 612 in the associated auto contour on/off handles 546, 548. Screws 606, 608 are screwed into threaded openings in the mounting pins 566, 568 to hold the head section release handles 536, 538 and the associated auto contour on/off handles 546, 548 in place. Retaining washers 616 shown in FIG. 9, are interposed between head portions of the screws 606, 608 and the upwardly-facing surfaces of the associated auto contour on/off handles 546, 548. The upwardly-facing surfaces of the auto contour on/off handles 546, 548 are countersunk around the central openings 612, as indicated by numeral 619, to avoid any projecting parts.

As shown in FIG. 8, the head section release handles 536, 538 and the auto contour on/off handles 546, 548 are dimensioned such that the grip portions 564 of the head section release handles 536, 538 and the grip portions 604 of the auto contour on/off handles 546, 548 are located near the corner portions 516, 518 so that a caregiver standing near the head end 32 of the stretcher 20 can have access to the grip portions 564 of the head section release handles 536, 538 and the grip portions 604 of the auto contour on/off handles 546, 548 through the cutouts 526, 528. The leg portions 552 of the head section release handles 536, 538 have apertures 572 near their respective distal ends for attaching associated cables 576, 578, which exit through associated openings 596, 598 (FIG. 9) in an upwardly extending flange 522 of the bottom panel 520. As shown diagrammatically in FIG. 8, the other ends of the cables 576, 578 are coupled to the trigger plate 136 (FIG. 5) of the gas spring 120 that is pivotally coupled to the head section 42 and pivotally coupled to the frame 26 as discussed above. The gas spring 120 is normally locked to prevent raising and lowering of the head section 42.

To release the gas spring 120, a caregiver pulls one of the head section release handles 536, 538 diagonally, longitudinally, or laterally toward the associated corner portion 516, 518. When pulled diagonally toward corner portions 516, 518, handles 536, 538 slide relative to respective posts 566, 568 and translate along the same direction as the orientation of respective slots 570. If handles 536, 538 are pulled longitudinally or laterally toward the associated corner portion 516, 518, then handles 536, 538 pivot about respective posts 566, 568 in one direction or the other. Handles 536, 538 may be pulled in any intermediate directions between the longitudinal and lateral directions which may result in a combination of pivoting and translational movement relative to respective posts 566, 568. As the head section release handle 536, 538 is pulled toward the respective corner portion 516, 518, regardless of the direction, the associated cable 576, 578 is pulled toward the head end 32 to unlock the gas spring 120 and unlock the head section 42 to pivot about its pivot axis 50. Guide rollers 586, 588 are mounted on the bottom panel 520 for guiding the cables 576, 578 to the openings 596, 598 in the upwardly extending flange 522 of the bottom panel 520.

The handle portions 602 of the auto contour on/off handles 546, 548 are movable from "on" or locking positions shown in solid in FIG. 8 near the head end strut 502 to "off" or releasing positions shown in phantom in FIG. 8 near the associated side struts 506, 508. A connecting link 650 connects the two auto contour on/off handles 546, 548 so that as one of the handles 546, 548 moves from its on position to its off position the other of the handles 546, 548 also moves from its on position to its off position. Likewise, as one of the handles 546, 548 moves from its off position to its on position the other of the handles 546, 548 also moves from its off position to its on position due to the interconnection of handles 546, 548 by link 650. Illustratively, the ends of link 650 are coupled to handles 546, 548 for pivoting movement about associated pins 652, 654. As shown in FIG. 8, the link 650 extends generally parallel to the head end strut 502. The points of coupling of link 650 to handles 546, 548 are such that handles 546, 548 rotate in opposite directions when moving from the on position to the off position, or vice versa. Thus, when one of handles 546, 548 rotates in a clockwise direction, the other of handles 546, 548 rotates in a counterclockwise direction, and vice versa.

As shown in FIGS. 8 and 9, an L-shaped rocker arm 620 (also referred to as the auto contour release lever) has a cylindrical body portion 622 and long and short arm portions 624, 626 that extend outwardly from the cylindrical body portion 622. In the illustrated embodiment, the two arm portions 624, 626 are substantially perpendicular to each other. The cylindrical body portion 622 of the rocker arm 620 has a central opening 628 for receiving a mounting pin 630 that extends upwardly from the bottom panel 520 of the head section 42. A screw 632 is screwed into a threaded opening in the mounting pin 630 to hold the rocker arm 620 in place. A retaining washer 634 is interposed between a head portion of the screw 632 and the upwardly-facing surface of the rocker arm 620. The long arm portion 624 has an elongate slot 636 near its free end for receiving a pin 638 that extends downwardly from the link 650, which connects the two auto contour on/off handles 546, 548. The pin 638 is located generally centrally relative to a length of the link 650. The short arm portion 626 has an aperture 640 for attachment of one end of a cable 672. As diagrammatically shown in FIG. 8, the other end of the cable 672 is coupled to the trigger plate 408 of the spring clutch 402 after exiting through an opening 674 in the upwardly extending flange 522 of the bottom panel 520. As mentioned above, the spring clutch 402 is normally locked to enable the auto contour mechanism 400.

As shown in FIG. 8, as the auto contour on/off handles 546, 548 move from their respective on positions to their respective off positions, the link 650, connecting the two handles 546, 548, moves laterally in a direction 642 (i.e., rightwardly as viewed from top in FIG. 8) from a first position closer to the side strut 508 to a second position closer to the side strut 506. As the link 650 moves in the direction 642, the downwardly-extending pin 638 causes the rocker arm 620 to rotate in a clockwise direction 644 from an on position tilted toward the side strut 508 to an off position tilted toward the side strut 506. The clockwise rotation of the rocker arm 620 causes the short arm 626 to pull the cable 672 toward the head end 32 in a direction 646 to release or unlock the spring clutch 402 to disable the auto contour mechanism 400.

As shown in FIG. 8, a retaining pin 656 extends upwardly from the bottom panel 520 of the head section 42 to maintain the rocker arm 620, and, therefore, the auto contour on/off handles 546, 548, in their respective off positions. The long arm portion 624 of the rocker arm 620 has a relatively stiff cantilevered detent member 658 near its free end. The cantilevered detent member 658 has an outwardly-facing groove 660 for receiving the pin 656 when the rocker arm 620 arrives at its off position. As indicated, the rocker arm 620 pivots in a clockwise direction 644 toward its off position as the auto contour on/off handles 546, 548 move to their respective off positions. As the rocker arm 620 approaches its off position, the retaining pin 656 passes an enlarged head portion of the detent member 658 to cause the detent member 658 to momentarily retract away from the retaining pin 656 to allow the rocker arm 620 to arrive at its off position. The detent member 658 then extends back toward the retaining pin 656 where the retaining pin 656 is received in the outwardly-facing groove 660 in the rocker arm 620 to lock the rocker arm 620, and, therefore, the auto contour on/off handles 546, 548, in their respective off positions shown in phantom in FIG. 8. In addition, an audible and tactile feedback is provided to the caregiver as the retaining pin 656 snaps into the groove 660 in the detent member 658.

The sequence is reversed when the auto contour on/off handles 546, 548 move from their respective off positions to their respective on positions. Thus, as the auto contour on/off handles 546, 548 move from their respective off positions to their respective on positions, the link 650, connecting the two handles 546, 548, moves in an opposite direction 643 (i.e., leftwardly as viewed from top in FIG. 8) from the second position closer to the side strut 506 to the first position closer to the side strut 508. As the link 650 moves in the direction 643, the pin 638 (FIG. 9), received in the elongate slot 636 (FIG. 9) in the rocker arm 620, causes the rocker arm 620 to rotate in a counterclockwise direction 645 from its off position tilted toward the side strut 506 to its on position tilted toward the side strut 508. The counterclockwise rotation of the rocker arm 620 causes the short arm 626 to release the cable 672 to relock the spring clutch 402 to enable the auto contour mechanism 400. The spring bias of the spring clutch 402 toward its locking position acts through the cable 672 to bias the rocker arm 620, and, therefore, the auto contour on/off handles 546, 548, toward their respective on positions shown in FIG. 8.

As shown in FIG. 11, circular portion 600 of handle 546 has two notches 664, 666 that correspond to the on and off positions thereof. As shown in FIGS. 8-9 and 12-13, an auto contour lockout lever 700 is coupled for pivoting movement to a pair of longitudinally-spaced flanges 522, 524 that extend upwardly from the bottom panel 520 by a longitudinally extending pin 702. The lockout lever 700 pivots between a locking position shown in FIG. 12 when the head section 42 is raised relative to frame 26 and a releasing position shown in FIG. 13 when the head section 42 is lowered fully relative to frame 26. The pivot pin 702 has a threaded portion that is screwed into a nut 704 to secure the lockout lever 700 to the upwardly extending flanges 522, 524.

Figure 12:
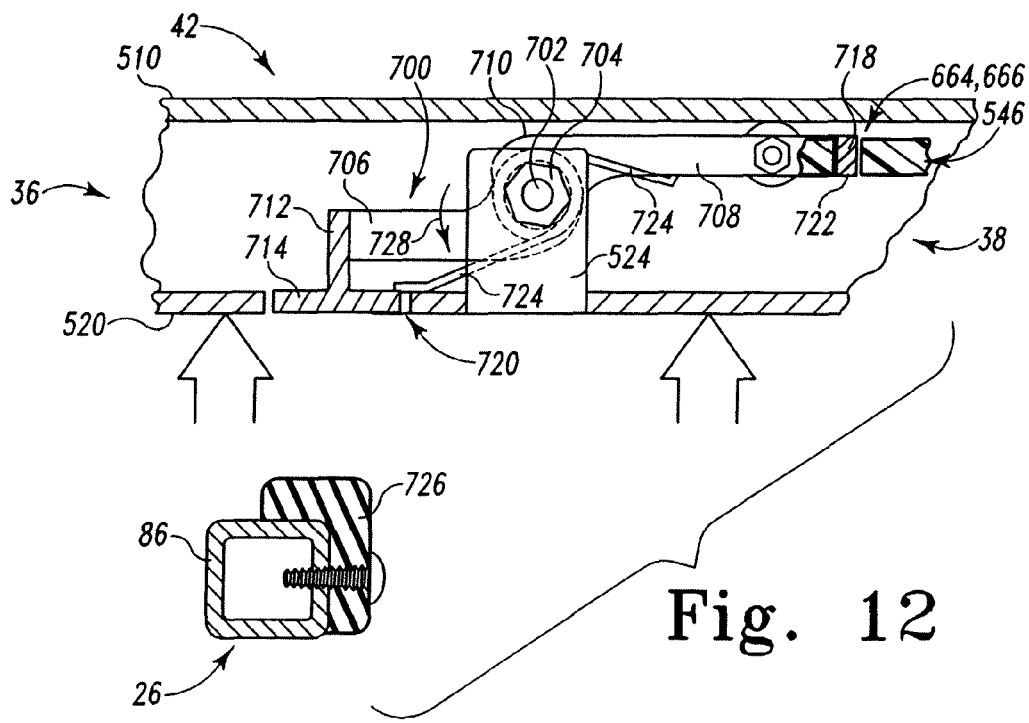
FIG. 12 is a sectional view, taken along the line 12-12 of FIG. 8, showing the auto contour lockout lever engaged with an associated auto contour on/off handle when the head section is raised away from a post extending upwardly from a frame member of the upper frame.
Figure 13:
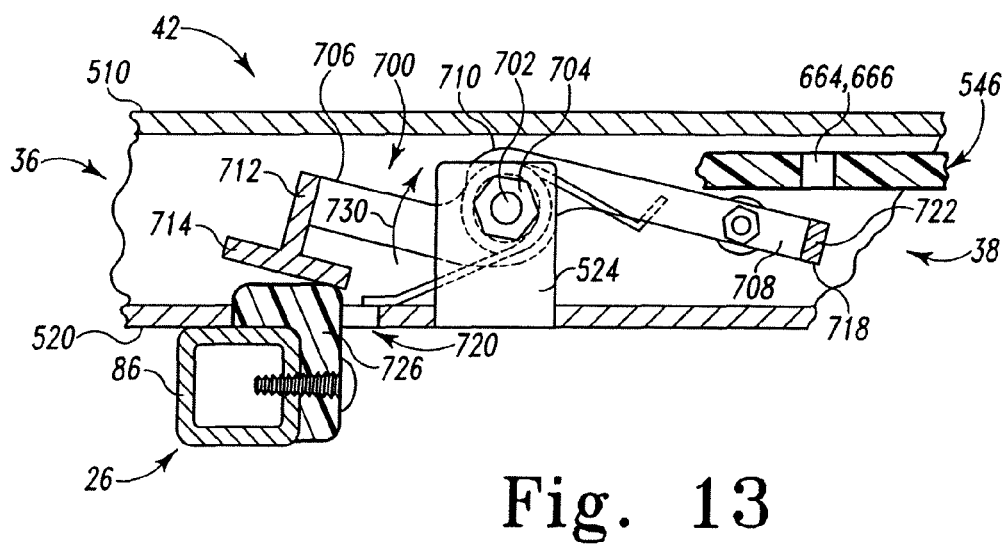
FIG. 13 is an end elevation view, similar to FIG. 12, showing the auto contour lockout lever pivoted by the post to a releasing position disengaged from the associated auto contour on/off handle when the head section is in the lowered position.

The lockout lever 700 has a central portion 710, a side portion 706 that extends laterally outwardly from the central portion 710 and a side portion 708 that extends laterally inwardly from the central portion 710. An end portion 712 of the outwardly extending side portion 706 is bent toward the head end 32 of head section 42. A block 714 is secured to the bent portion 712 by a pair of laterally-spaced flanges 716 that extend upwardly from the block 714. An end portion 718 of the inwardly extending side portion 708 is also bent toward the head end 32 of head section 42. The lockout lever 700 has a generally U-shaped configuration in plan view as shown in FIGS. 8 and 9, and a generally S-shaped configuration in end view as shown in FIGS. 12 and 13. A spacer 711 is provided between the central portion 710 of lever 700 and flange 522. Pin 702 extends through a bore of spacer 711.

When the lockout lever 700 is in the locking position, shown in FIG. 12, the block 714 is received in a cutout 720 in the bottom panel 520 such that the downwardly-facing surface of the block 714 is generally coplanar with the downwardly-facing surface of the bottom panel 520 and a terminal portion 722 of the bent portion 718 of the lockout lever 700 is received in one of the two notches 664, 666 in the circular portion 600 of the auto contour on/off handle 546, depending upon whether the auto contour on/off handles 546, 548 are in their respective on positions as shown in solid in FIG. 8 or in their respective off positions as shown in phantom in FIG. 8. Thus, if the auto contour on/off handles 546, 548 are in their respective on positions, the terminal portion 722 of the lockout lever 700 is received in the notch 664 in the circular portion 600 of the auto contour on/off handle 546 to lock the handles 546, 548 in their respective on positions. Likewise, if the auto contour on/off handles 546, 548 are in their respective off positions, the terminal portion 722 of the lockout lever 700 is received in the notch 666 in the circular portion 600 of the auto contour on/off handle 546 to lock the handles 546, 548 in their respective off positions. A torsion spring 724 biases the lockout lever 700 in a direction 728 toward its locking position shown in FIG. 12. In the illustrated embodiment, both the block 714 and the cutout 720 have a generally rectangular cross section.

As the head section 42 is lowered to its fully lowered position, a post or block 726 coupled to the upper frame 26 enters the cutout 720 in the bottom panel 520 from a lower side thereof as shown in FIG. 13 to pivot the lockout lever 700 in a direction 730 disengaging the terminal portion 722 of the lockout lever 700 from the associated notch 664, 666 to free the auto contour on/off handles 546, 548 for movement between the on and off positions. If desired, the auto contour on/off handles 546, 548 can then be moved from their on positions to their off positions or from their off positions to their on positions. When the auto contour on/off handles 546, 548 are moved from their off positions to their on positions, the spring bias of the spring clutch 402 toward its locking position acts through the cable 672 to bias the rocker arm 620, and, therefore, the auto contour on/off handles 546, 548, toward their respective on positions shown in solid in FIG. 8 until the head section 42 is raised and the terminal portion 722 of the lockout lever 700 is again received in the notch 664 in the auto contour on/off handle 546. On the other hand, when the auto contour on/off handles 546, 548 are moved from their on positions to their off positions, the cantilevered detent member 658 holds the rocker arm 620, and, therefore, the auto contour on/off handles 546, 548, in their respective off positions shown in phantom in FIG. 8 until the head section 42 is raised and the terminal portion 722 of the lockout lever 700 is again received in the notch 666 in the auto contour on/off handle 546.

When the head section 42 is raised while the spring clutch 402 is released (auto contour feature disabled) as shown in FIG. 14, the downwardly extending flanges 196 (FIG. 6) of the head section 42 still cause the clutch housing 404 (FIG. 6) to move toward the head end 32. However, the connecting rod 406, the cam bracket 420 and the cam 450 mounted on the cam bracket 420 (all shown in FIG. 6) do not move toward the head end 32. Instead, the thigh section 46, which remains substantially coplanar with the seat section 44, pushes down on the roller assembly 460 (FIG. 6). The thigh section 46 is spring loaded toward its coplanar position by a compression spring 378 shown in FIG. 15. As shown in FIG. 15, the compression spring 378 is held in a state of compression between a pin 380 that extends laterally outwardly from the tube 370 of the knee crank mechanism 360 and a pin 374 that extends laterally outwardly from the flanges 376 that extend downwardly from the underside of the thigh section 46. As the roller assembly 460 is pushed down, the bottom roller 480, which is in engagement with the steep inclined portion 452 of the cam 450, pushes the cam bracket 420 toward the foot end 34 of stretcher 20, thereby compressing a coiled reset spring 488 shown in FIGS. 5-7 and 14.

As shown in FIGS. 5, 7 and 14, the reset spring 488 is compressed between a flange 490 coupled to the underside of the cam bracket 420 and a block 492 which is positioned next to one of the rollers 439 that supports the cam bracket 420 relative to the flanges 442. A pin 493, shown best in FIG. 7 (in phantom), is fastened to the flange 490 and extends longitudinally therefrom through the bore of the spring 488 and into a bore formed in the block 492. As the spring 488 is compressed, the roller 439, which is adjacent to the block 492 and which is coupled to the flanges 442 that are fixed in place relative to the frame 26, prevents the block 492 from moving toward the foot end 34 of the stretcher 20 and the pin 493 moves further into the bore of the block 490. Receipt of a portion of pin 493 in the bore of the block 492 prevents the block 490 from falling downwardly out of the channel provided in cam bracket 420.

When the head section 42 is moved back to its lowered position while the spring clutch 402 is released, the compressed reset spring 488 returns the cam bracket 420, and the cam 450 mounted thereon, to their respective home positions shown in FIG. 2. As shown in FIG. 6, another reset spring 494 is coupled to the roller assembly 460 and coupled to one of the flanges 442 to bias the roller assembly 460 upwardly. When the head section 42 is moved back to its lowered position, the reset spring 494 returns the roller assembly 460 from its lowered position shown in FIG. 14 to its raised position shown in FIG. 2.

Although certain illustrative embodiments have been described in detail above, variations and modifications exist within the scope and spirit of this disclosure as described and as defined in the following claims.

The invention claimed is:

1. A patient support apparatus comprising
   a frame,
   a seat section supported by the frame,
   a thigh section situated adjacent the seat section,
   a head section coupled to the frame and being raiseable and lowerable relative to the frame,
   a linkage coupled to the head, seat, and thigh sections, the linkage having a first mode of operation in which the seat and thigh sections remain substantially parallel to each other as the head section is raised and lowered, and the linkage having a second mode of operation in which the thigh section tilts relative to the seat section as the head section is raised and lowered, and
   a handle coupled to the head section and coupled to the linkage, the handle being movable relative to the head section between a first position in which the linkage is in the first mode of operation and a second position in which the linkage is in the second mode of operation, wherein the linkage comprises a cam supported by the frame, the linkage comprises a roller assembly interposed between the thigh section and the cam, and the cam moves beneath the roller assembly to move the roller assembly thereby to tilt the thigh section relative to the seat section.

2. The apparatus of claim 1, wherein the head section is movable between a lowered position in which the head section is generally horizontal and a raised position in which the head section is generally upright and nearly vertical, the head section having an intermediate position between the raised position and the lowered position, and when the linkage is in the second mode of operation, the thigh section moves relative to seat section from a first position generally parallel to the seat section to a second position raised upwardly relative to the seat section as the head section moves from the lowered position to the intermediate position and the thigh section moves relative to the seat section from the second position back to the first position as the head section moves from the intermediate position to the raised position.

3. The apparatus of claim 2, wherein an angle between the head section and the frame is about 50 degrees when the head section is in the intermediate position.

4. The apparatus of claim 2, wherein an angle between the head section and the frame is about 80 degrees when the head section is in the raised position.

5. The apparatus of claim 2, wherein an angle between the thigh section and the seat section rail is about 20 degrees when the head section is in the intermediate position.

6. The apparatus of claim 1, wherein the cam has a first portion that moves beneath the roller assembly to raise the thigh section as the head section moves upwardly from a lowered position generally parallel to the frame to an intermediate position, and the cam has a second portion that moves beneath the roller assembly to lower the thigh section as the head section moves further upwardly from the intermediate position to a raised position.

7. The apparatus of claim 6, wherein the roller assembly is coupled to the frame for movement in a generally vertical direction, the roller assembly includes a top roller positioned to contact the thigh section, and the roller assembly includes a bottom roller positioned to contact the cam.

8. The apparatus of claim 1, wherein the linkage comprises a lockable device coupling the cam to the head section, the lockable device being locked when the linkage is in the second mode of operation so that raising and lowering of the head section moves the cam beneath the roller assembly, and the lockable device being unlocked when the linkage is in the first mode of operation so that the cam remains generally stationary beneath the roller assembly as the head section is raised and lowered.

9. The apparatus of claim 8, wherein the lockable device is locked when the handle is in the second position and the lockable device is unlocked when the handle is in the first position.

10. The apparatus of claim 9, further comprising a member and the at least one handle being configured to move the member to unlock the lockable device when the at least one handle moves from its second position to its first position.

11. The apparatus of claim 10, further comprising a cable coupled to the member and coupled to the lockable device such that movement of the member pulls the cable to unlock the lockable device to decouple the head section from the cam when the at least one handle moves from its second position to its first position.

12. The apparatus of claim 1, wherein the head section includes a panel having a pair of corner portions near a head end, the handle comprises a pair of handles coupled to the panel adjacent the respective corner portions, the pair of handles are coupled together by a link so that movement of a first one of the handles from its first position to its second position results in movement of a second one of the handles from its first position to its second position.

13. A patient support apparatus comprising
a frame,
a seat section supported by the frame,
a thigh section situated adjacent the seat section,
a head section coupled to the frame and being raiseable and lowerable relative to the frame,
a linkage coupled to the head, seat, and thigh sections, the linkage having a first mode of operation in which the seat and thigh sections remain substantially parallel to each other as the head section is raised and lowered, and the linkage having a second mode of operation in which the thigh section tilts relative to the seat section as the head section is raised and lowered, and
a handle coupled to the head section and coupled to the linkage, the handle being movable relative to the head section between a first position in which the linkage is in the first mode of operation and a second position in which the linkage is in the second mode of operation, wherein the handle includes a generally circular portion having first and second notches corresponding to the first and second positions of the handle, respectively, and further comprising a locking member coupled to the head section and a spring biasing a locking portion of the locking member into one of the two notches in the associated circular portion to prevent the handle from moving when the head section is raised.

14. The apparatus of claim 13, further comprising a post extending from the frame to displace the locking member to disengage the locking portion from the associated notch in the circular portion to free the handle for movement when the head section is moved to the lowered position.

15. The apparatus of claim 1, further comprising an actuator coupled to the head section and coupled to the frame, the actuator being lockable to prevent tilting movement of the head section relative to the frame and the actuator being releasable to allow pivoting movement of the head section relative to the frame, and at least one head section release handle coupled to the head section and movable in a plurality of directions between a locking position and a plurality of releasing positions, wherein movement of the at least one head section release handle from the locking position to any of the plurality of releasing positions releases the actuator to permit tilting of the head section relative to the frame.

16. A patient support apparatus comprising
a frame,
a seat section supported by the frame,
a thigh section situated adjacent the seat section,
a head section coupled to the frame and being raiseable and lowerable relative to the frame,
a linkage coupled to the head, seat, and thigh sections, the linkage having a first mode of operation in which the seat and thigh sections remain substantially parallel to each other as the head section is raised and lowered, and the linkage having a second mode of operation in which the thigh section tilts relative to the seat section as the head section is raised and lowered,
a handle coupled to the head section and coupled to the linkage, the handle being movable relative to the head section between a first position in which the linkage is in the first mode of operation and a second position in which the linkage is in the second mode of operation, and
an actuator coupled to the head section and coupled to the frame, the actuator being lockable to prevent tilting movement of the head section relative to the frame and the actuator being releasable to allow pivoting movement of the head section relative to the frame, and at least one head section release handle coupled to the head section and movable in a plurality of directions between a locking position and a plurality of releasing positions, wherein movement of the at least one head section release handle from the locking position to any of the plurality of releasing positions releases the actuator to permit tilting of the head section relative to the frame, wherein the head section release handle comprises a main body portion with a hand grip and a leg portion extending from the main body portion, the leg portion having an elongated slot, and the head section has a pin received in the slot.

17. The apparatus of claim 1, wherein the head section includes a head section frame having a pair of corner regions and a panel coupled to the head section frame, the panel has cutouts adjacent the corner regions of the head section frame, and at least a portion of the handle is accessible through one of the cutouts in the panel.

18. The apparatus of claim 17, wherein the handle is rotatably coupled to the panel.

19. A patient support apparatus comprising
a frame,
a seat section supported by the frame,
a thigh section situated adjacent the seat section,
a head section coupled to the frame and being raiseable and lowerable relative to the frame,
a linkage coupled to the head, seat, and thigh sections, the linkage having a first mode of operation in which the seat and thigh sections remain substantially parallel to each other as the head section is raised and lowered, and the linkage having a second mode of operation in which the thigh section tilts relative to the seat section as the head section is raised and lowered, and
a handle coupled to the head section and coupled to the linkage, the handle being movable relative to the head section between a first position in which the linkage is in the first mode of operation and a second position in which the linkage is in the second mode of operation, wherein the head section includes a head section frame having a pair of corner regions and a panel coupled to the head section frame, the panel has cutouts adjacent the corner regions of the head section frame, and at least a portion of the handle is accessible through one of the cutouts in the panel, wherein the handle comprises a pair of handles, each handle of the pair of handles being adjacent a respective corner region of the pair of corner regions, each handle being rotatably coupled to the panel, and further comprising a link interconnecting the pair of handles such that the handles are constrained to rotate in opposite directions relative to the panel.

* * * * *